(12) United States Patent
Grimmelbein

(10) Patent No.: US 11,642,507 B2
(45) Date of Patent: May 9, 2023

(54) NEEDLE MODULES AND ASSOCIATED METHODS

(71) Applicant: Black Claw LLC, Portland, OR (US)

(72) Inventor: Brett A. Grimmelbein, San Francisco, CA (US)

(73) Assignee: Black Claw LLC, Portland, OR (US)

( * ) Notice: Subject to any disclaimer, the term of this patent is extended or adjusted under 35 U.S.C. 154(b) by 0 days.

(21) Appl. No.: 17/121,294

(22) Filed: Dec. 14, 2020

(65) Prior Publication Data
US 2022/0184365 A1 Jun. 16, 2022

(51) Int. Cl.
*A61M 37/00* (2006.01)

(52) U.S. Cl.
CPC ..... *A61M 37/0076* (2013.01); *A61M 2207/00* (2013.01)

(58) Field of Classification Search
CPC ......... A61M 37/0076–0084; A01K 11/00–008
See application file for complete search history.

(56) References Cited

U.S. PATENT DOCUMENTS

| 5,551,319 | A | * | 9/1996 | Spaulding | B43K 8/22 30/362 |
|---|---|---|---|---|---|
| 9,050,445 | B2 | | 6/2015 | Klebs et al. | |
| 9,114,239 | B2 | | 8/2015 | Lee | |
| 2004/0186501 | A1 | * | 9/2004 | Su | A61M 37/0076 606/185 |
| 2008/0306502 | A1 | | 12/2008 | Lisec et al. | |
| 2012/0279330 | A1 | * | 11/2012 | Lin | A61M 37/0076 74/45 |

(Continued)

FOREIGN PATENT DOCUMENTS

| CN | 2493083 Y | 5/2002 |
|---|---|---|
| CN | 1864641 A | 11/2006 |

(Continued)

OTHER PUBLICATIONS

Joshua Bowers, "Needle Lag and Snag on Rotaries", www.joshuabowers.com/blog/2017/12/18/needle-lag-and-snag-on-rotaries#comments-5a3898a653450a3641058e31=, published Dec. 18, 2017.

(Continued)

*Primary Examiner* — Darwin P Erezo
*Assistant Examiner* — Brigid K Byrd
(74) *Attorney, Agent, or Firm* — Kolitch Romano Dascenzo Gates LLC

(57) ABSTRACT

Needle modules and associated methods. A needle module includes a module housing and a needle assembly operatively supported within the module housing. The module housing extends along a housing axis and includes a housing tip with a tip outlet. The needle assembly includes a drive bar extending at least partially along a drive bar axis and a needle grouping extending from the drive bar at least partially along a needle grouping axis and contacting the housing tip at a needle grouping contact location and at an angle relative to the housing tip at the needle grouping contact location. In examples, a method of assembling a needle module includes preparing a needle assembly that includes a needle grouping and a drive bar and installing the needle assembly within a module housing such that the needle grouping contacts the module housing at a needle grouping contact location.

21 Claims, 12 Drawing Sheets

(56) References Cited

U.S. PATENT DOCUMENTS

| | | | |
|---|---|---|---|
| 2013/0226211 A1 | 8/2013 | Xiao | |
| 2016/0184572 A1 | 6/2016 | Xiao | |
| 2017/0072178 A1 | 3/2017 | Xiao | |
| 2019/0060626 A1 | 2/2019 | Xiao | |
| 2019/0217072 A1* | 7/2019 | Xiao | ......... A61M 37/0084 |
| 2019/0366069 A1 | 12/2019 | Xiao | |
| 2020/0023175 A1* | 1/2020 | Xiao | ......... A61M 37/0084 |
| 2020/0276429 A1 | 9/2020 | Xiao | |

FOREIGN PATENT DOCUMENTS

| | | |
|---|---|---|
| CN | 201481464 U | 5/2010 |
| CN | 205814861 U | 12/2016 |
| DE | 202013102384 U1 | 8/2013 |
| EP | 3578224 A1 | 12/2019 |
| KR | 2020090004825 U | 5/2009 |
| KR | 101260511 B1 | 5/2013 |
| KR | 101805063 B1 | 12/2017 |
| WO | WO 2018202989 A1 | 11/2018 |

OTHER PUBLICATIONS

Mattitude, "Needle Bend", Help Me Tattoo Tattoo Training Forum, helpmetattoo.com/forums/threads/needle-bend.3376, published Aug. 18, 2012.

Tattoo University, "Needle Bending Tattoo University", YouTube, www.youtube.com/watch?v=Um7NcPSixH8, published Jan. 29, 2017.

Tattoosuperior1, "Proper Tattoo Machine Needle/Tube and Voltage Setup" YouTube, www.youtube.com/watch?v=ixDcsohKDd8, published Jul. 15, 2010.

English-language machine translation of Chinese Patent Application Publication No. CN 1864641 A, Nov. 22, 2006.

English-language machine translation of Chinese Patent No. CN 2493083 Y, May 29, 2002.

English-language machine translation of Chinese Patent No. CN 201481464 U, May 26, 2010.

English-language machine translation of Chinese Patent No. CN 205814861 U, Dec. 21, 2016.

English-language machine translation of German Patent Application Publication No. DE 202013102384 U1, Aug. 1, 2013.

English-language machine translation of European Patent Application Publication No. EP 3578224 A1, Dec. 11, 2019.

English-language machine translation of Korean Patent No. KR 101260511 B1, May 6, 2013.

English-language machine translation of Korean Patent No. KR 101805063 B1, Dec. 5, 2017.

English-language machine translation of Korean Patent No. KR 2020090004825 U, May 20, 2009.

English-language machine translation of PCT Patent Application Publication No. WO 2018202989 A1, Nov. 8, 2018.

* cited by examiner

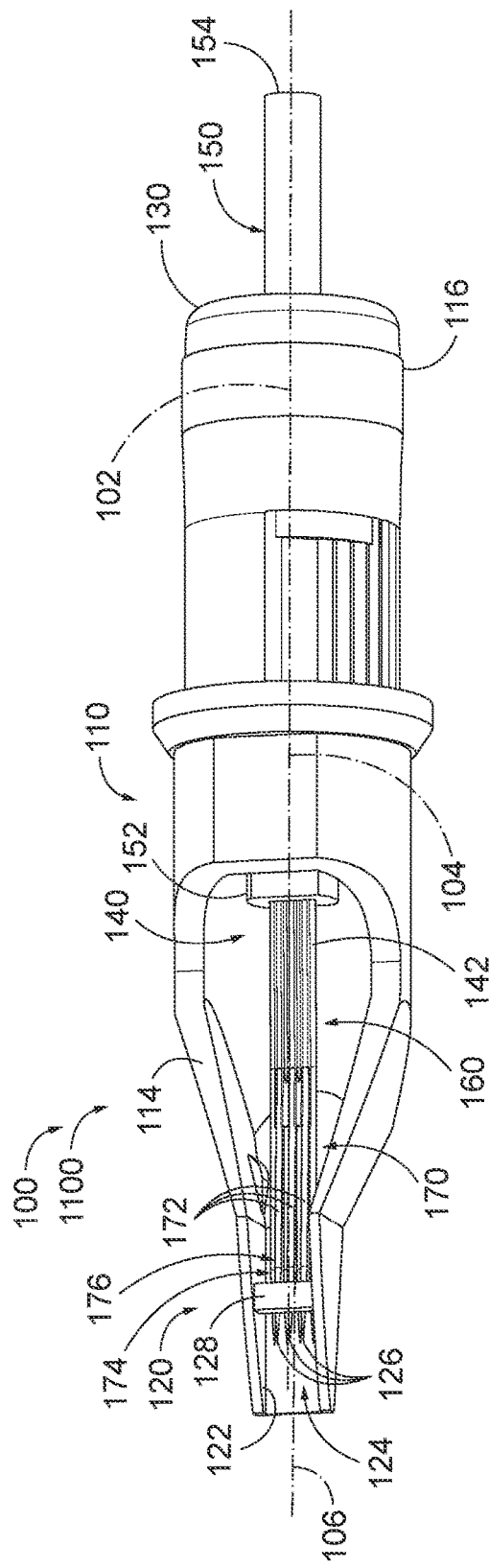

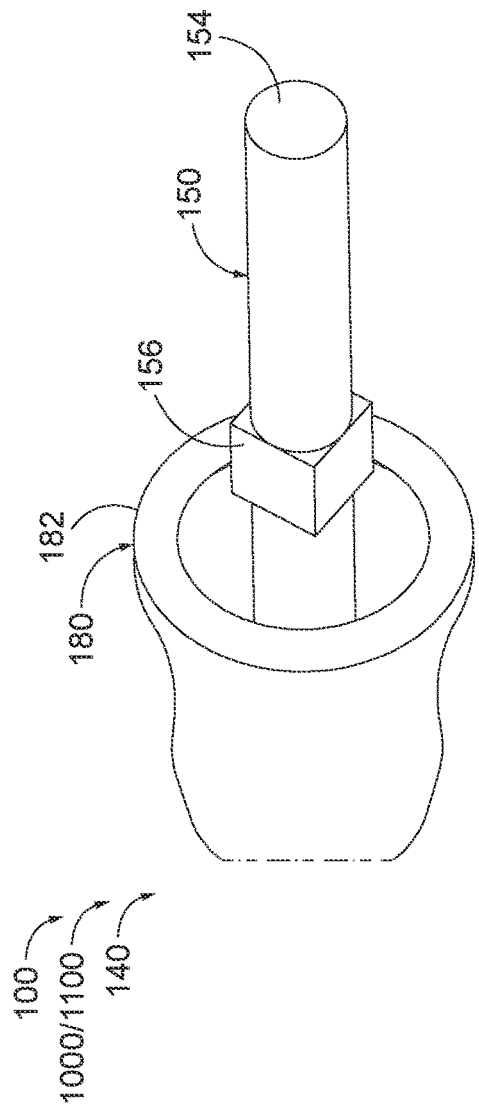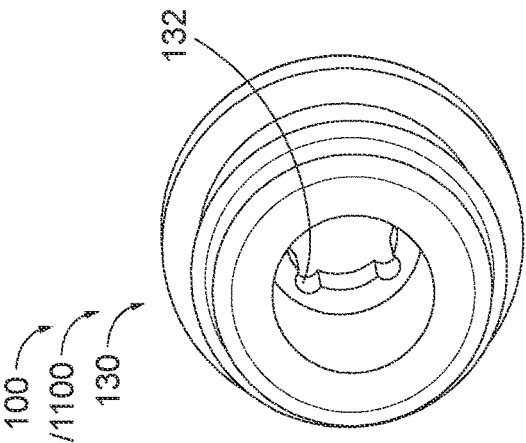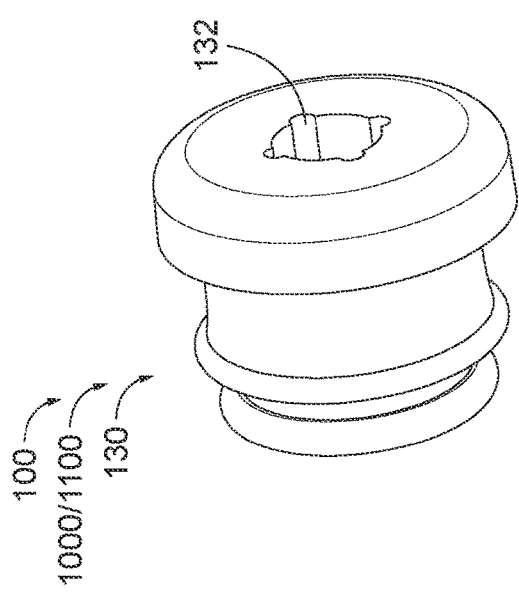

ced by examples of needle modules with a needle grouping attached to a drive bar at an angle and with a needle assembly in a retracted position according to the present disclosure.

NEEDLE MODULES AND ASSOCIATED METHODS

FIELD OF THE DISCLOSURE

The present disclosure relates to needle modules and associated methods.

BACKGROUND OF THE DISCLOSURE

To apply a tattoo or permanent makeup to a subject's skin, a tattoo artist typically employs a reciprocating needle to repeatedly puncture an upper layer of the subject's skin and to deliver an ink to the subject's skin. Traditional tattoo needle groupings attach directly to a reciprocating machine and extend through a needle tube that is gripped by the tattoo artist. However, care must be taken to ensure that the reciprocating machine is protected from bodily fluids that are released during the tattooing process. To facilitate such protection, some tattoo needle assemblies take the form of a self-contained and disposable needle module, or cartridge, that includes a module housing that is configured to be supported by the reciprocating machine and that is configured to fluidly separate the reciprocating machine from the needle grouping. In some examples, a flow of ink from the needle module to the subject's skin is augmented via capillary action generated by an interface between the needle grouping and the module housing.

SUMMARY OF THE DISCLOSURE

Needle modules and associated methods are disclosed herein. A needle module for applying ink to skin of a subject includes a module housing and a needle assembly operatively supported within the module housing. The module housing includes, or defines, an ink reservoir. The module housing extends along and defines a housing axis and includes a housing tip that defines a tip outlet, and the housing axis extends through the housing tip. The needle assembly includes a drive bar extending at least partially along a drive bar axis and a needle grouping extending from the drive bar at least partially along a needle grouping axis. The needle grouping includes one or more needles. The needle assembly is configured to reciprocate along the drive bar axis such that at least a portion of the needle grouping reciprocates into and out of the module housing via the tip outlet. The needle grouping contacts the housing tip at a needle grouping contact location as the needle grouping reciprocates into and out of the module housing, and the needle grouping is angled relative to the housing tip at the needle grouping contact location at least when the needle grouping extends out of the module housing.

In some examples, a method of assembling a needle module includes preparing a needle assembly that includes a needle grouping operatively coupled to a drive bar and installing the needle assembly within a module housing. In particular, the installing the needle assembly within the module housing includes installing such that at least a portion of the needle grouping is configured to reciprocate into and out of the module housing and such that the needle grouping contacts the module housing at a needle grouping contact location as the needle grouping reciprocates into and out of the module housing. The preparing the needle assembly includes preparing such that at least a portion of the needle grouping extends along a needle grouping axis that deviates, by a needle grouping bias angle, from a drive bar axis along which at least a portion of the drive bar extends.

The needle grouping bias angle may be measured between the needle grouping axis and the drive bar axis, and may be at least 1 degree and at most 5 degrees. The preparing the needle assembly is performed prior to the installing the needle assembly within the module housing.

BRIEF DESCRIPTION OF THE DRAWINGS

FIG. 15 is a top plan view of a second example needle module with a needle assembly in a retracted position according to the present disclosure.

FIG. 16 is a top plan view of the second example needle module of FIG. 15, with the needle assembly in an extended position according to the present disclosure.

FIG. 20 is a rear top side perspective view of an example of a drive bar including a drive bar locator according to the present disclosure.

FIG. 21 is a rear side perspective view of an example of a housing cap according to the present disclosure.

FIG. 22 is a front side perspective view of the housing cap of FIG. 21.

DETAILED DESCRIPTION

Figure 1:
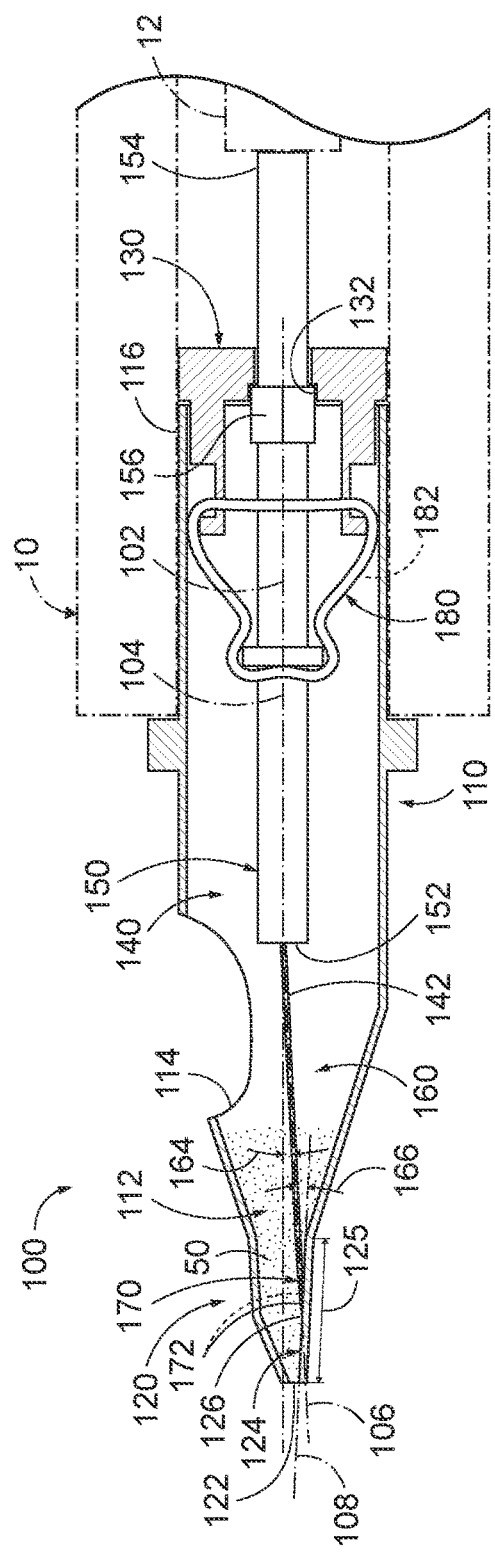
FIG. 1 is a schematic cross-sectional side elevation view representing examples of needle modules with a needle grouping attached to a drive bar at an angle and with a needle assembly in a retracted position according to the present disclosure.

FIGS. 1-23 provide examples of needle modules 100 and/or of methods 200 of assembling needle modules 100 according to the present disclosure. Elements that serve a similar, or at least substantially similar, purpose are labeled with like numbers in each of FIGS. 1-23, and these elements may not be discussed in detail herein with reference to each of FIGS. 1-23. Similarly, all elements may not be labeled in each of FIGS. 1-23, but reference numerals associated therewith may be utilized herein for consistency. Elements, components, and/or features that are discussed herein with reference to one or more of FIGS. 1-23 may be included in and/or utilized with any of FIGS. 1-23 without departing from the scope of the present disclosure.

In general, in the Figures, elements that are likely to be included in a given (i.e., a particular) embodiment are illustrated in solid lines, while elements that are optional to a given embodiment are illustrated in dashed lines. However, elements that are shown in solid lines are not essential to all embodiments, and an element shown in solid lines may be omitted from a given embodiment without departing from the scope of the present disclosure.

Figure 7:
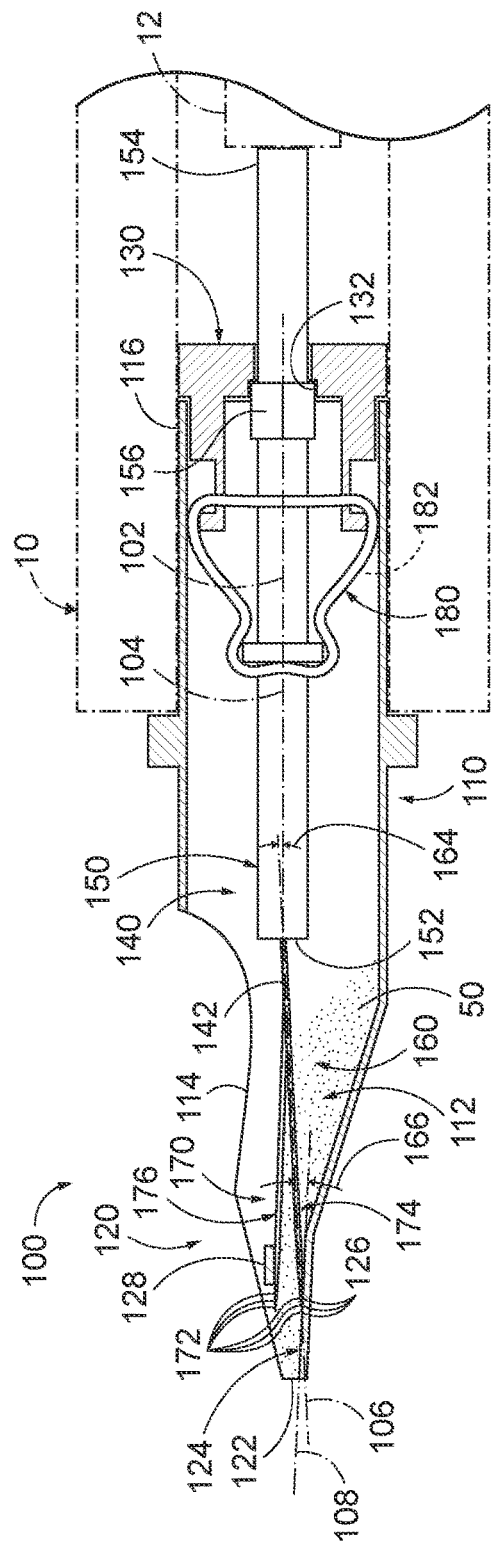
FIG. 7 is a schematic cross-sectional side elevation view representing examples of needle modules with a needle grouping that includes a first needle subset and a second needle subset and with a needle assembly in a retracted position according to the present disclosure.
Figure 8:
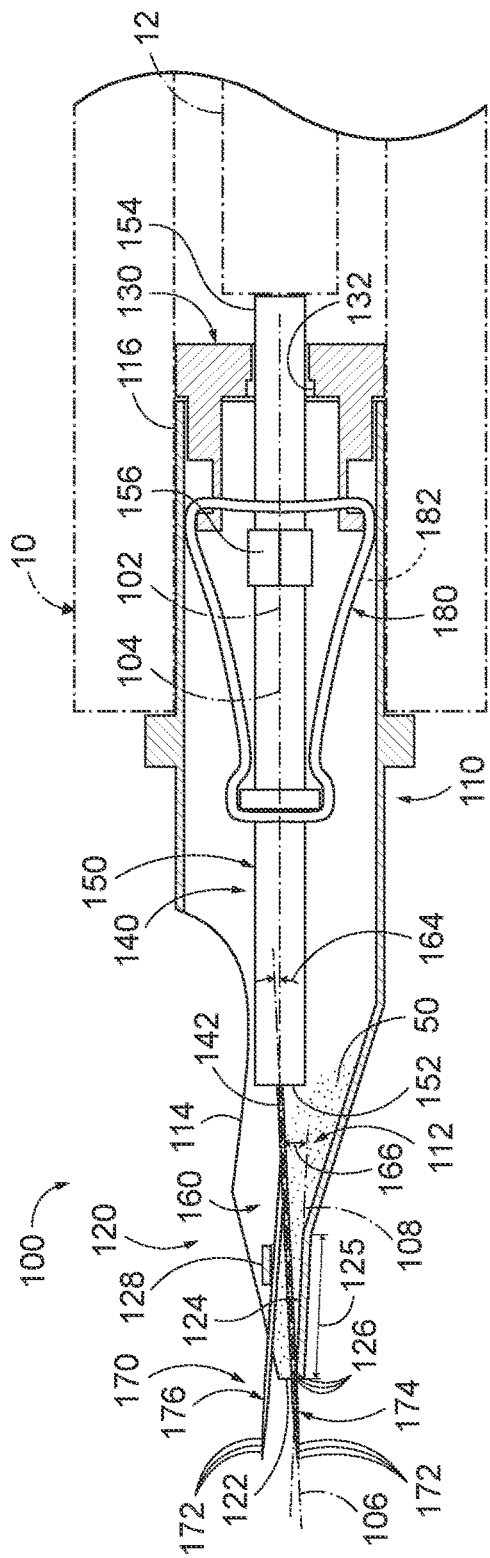
FIG. 8 is a schematic cross-sectional side elevation view representing the example needle modules of FIG. 7, with the needle assembly in an extended position according to the present disclosure.
Figure 9:
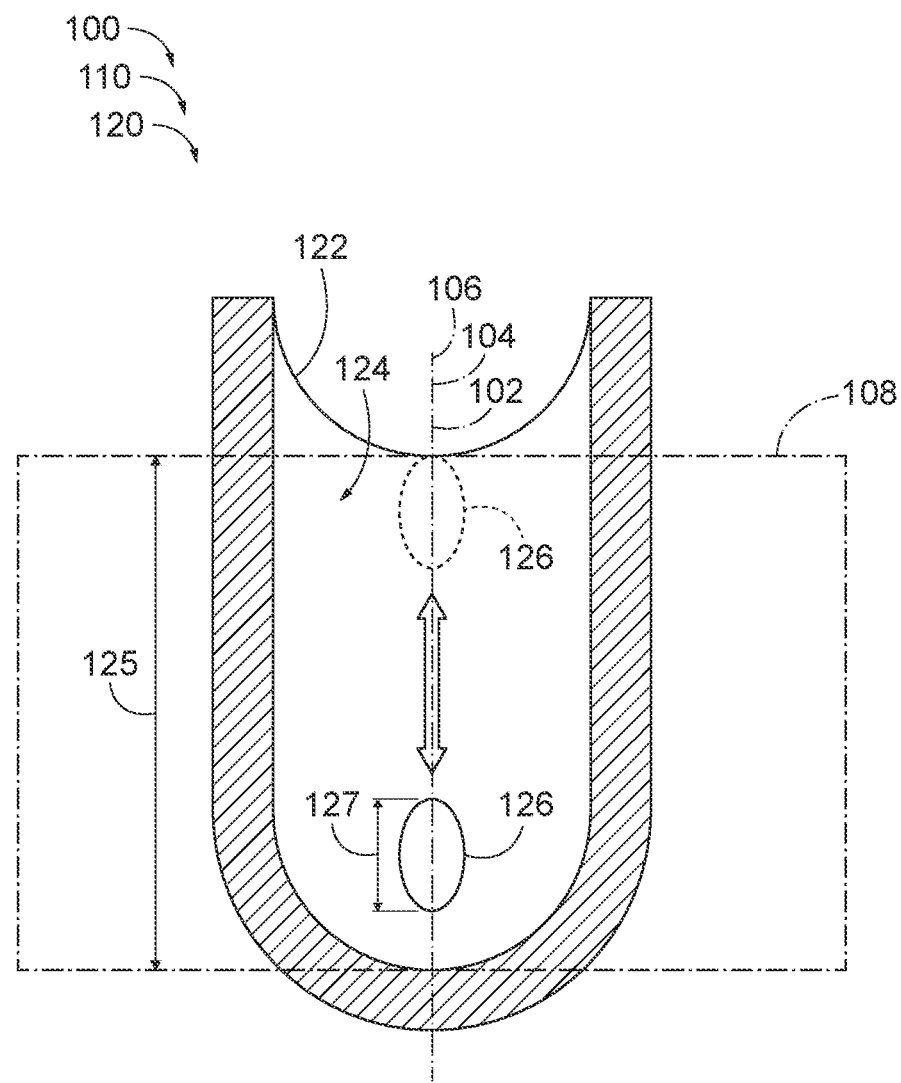
FIG. 9 is a schematic cross-sectional top rear isometric view of a portion of an example of a housing tip according to the present disclosure.
Figure 10:
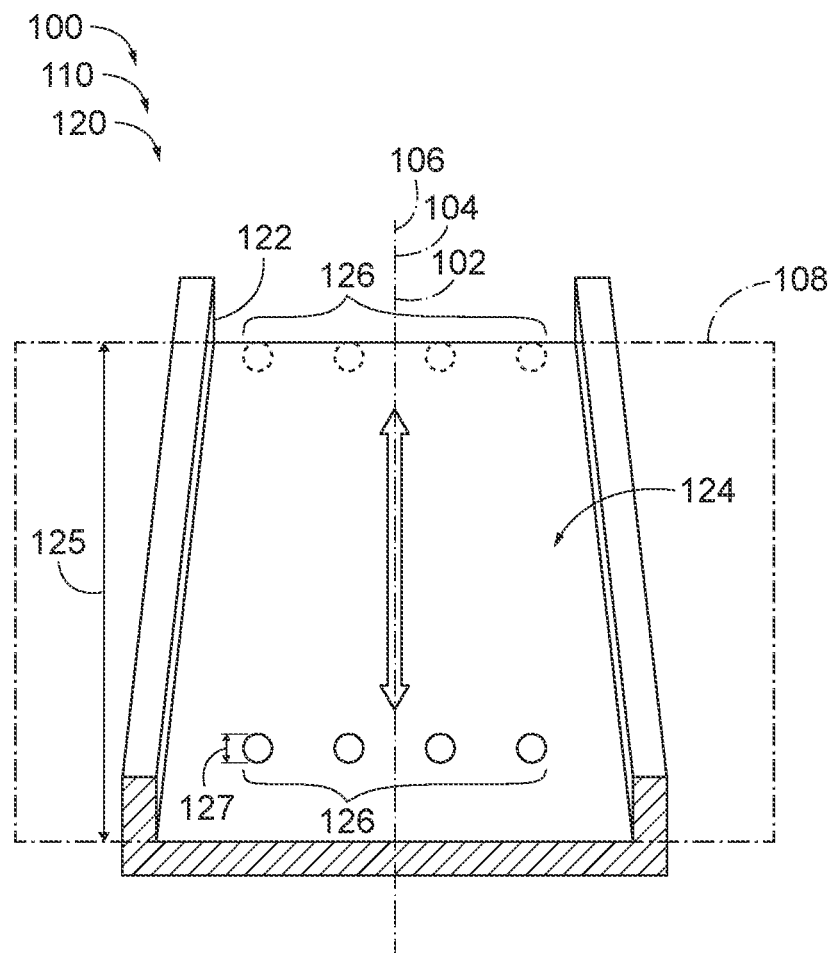
FIG. 10 is another schematic cross-sectional top rear isometric view of a portion of an example of a housing tip according to the present disclosure.
Figure 11:
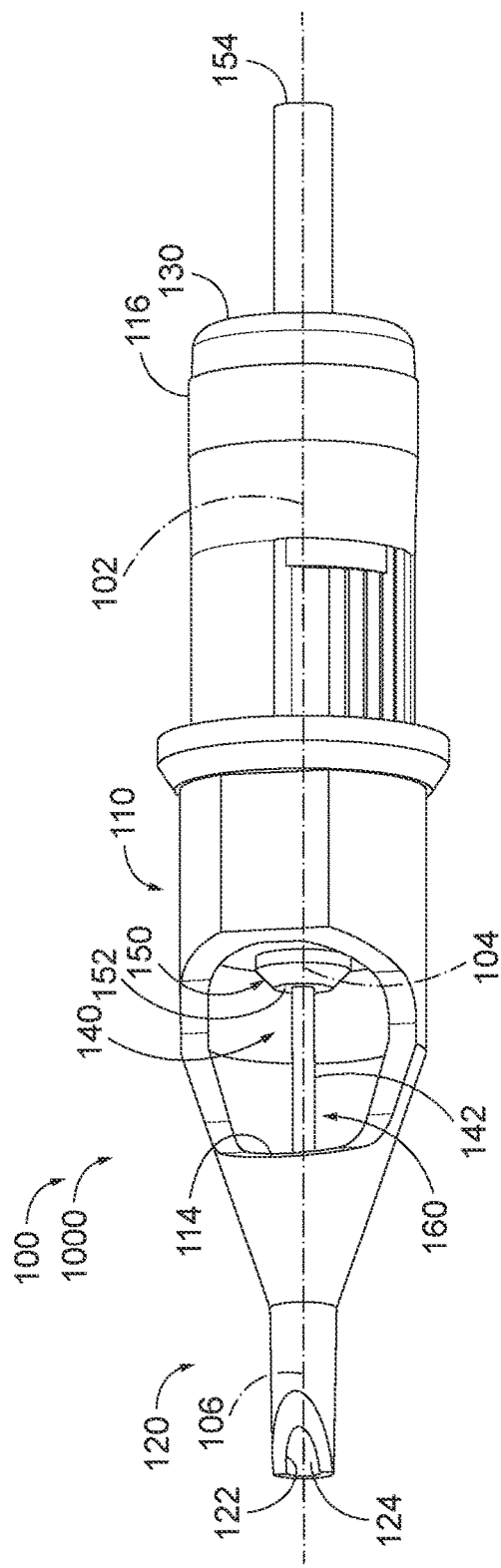
FIG. 11 is a top view of a first example needle module with a needle assembly in a retracted position according to the present disclosure.
Figure 12:
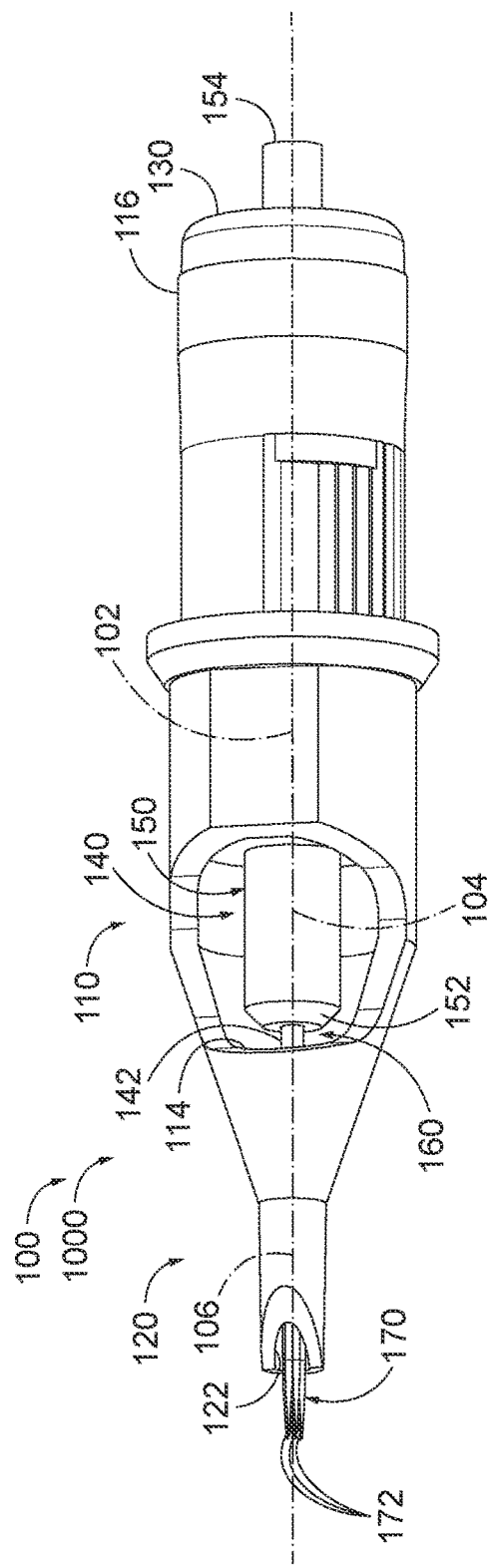
FIG. 12 is a top view of the first example needle module of FIG. 11, with the needle assembly in an extended position according to the present disclosure.
Figure 13:
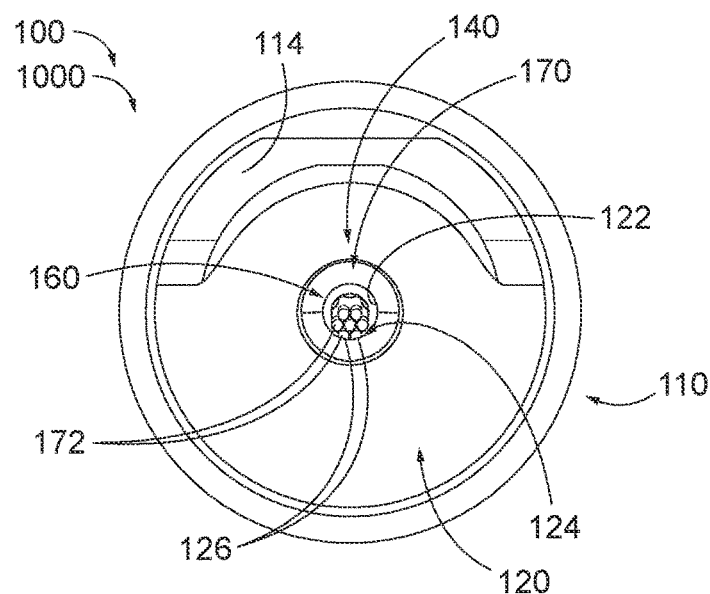
FIG. 13 is a front view of the first example needle module of FIGS. 11-12, with the needle assembly in the retracted position.
Figure 14:
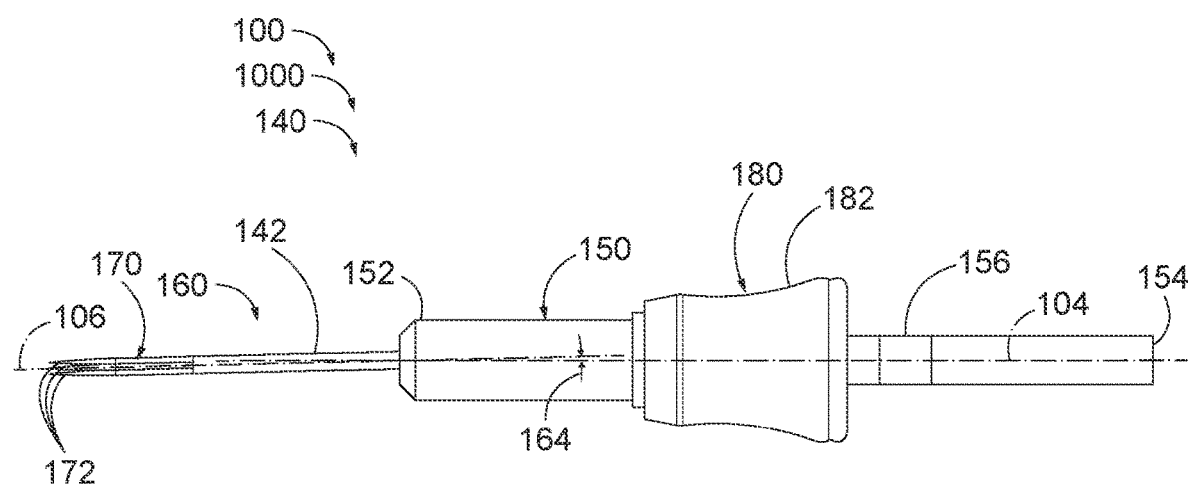
FIG. 14 is a side elevation view of the needle assembly of the first example needle module of FIGS. 11-13.

FIGS. 1-10 are schematic cross-sectional illustrations of examples of needle modules 100 according to the present disclosure and/or portions thereof. In particular, FIGS. 1-2, FIGS. 3-4, FIGS. 5-6, and FIGS. 7-8 respectively represent four examples of configurations of needle modules 100, as described in more detail herein, while FIGS. 9-10 represent portions of needle modules 100, such as those schematically illustrated in FIGS. 1-8. FIGS. 11-22 are less schematic illustrations of more specific examples of needle modules 100. In particular, FIGS. 11-14 illustrate aspects of a first example needle module 1000, while FIGS. 15-19 illustrate aspects of a second example needle module 1100, and FIGS. 20-22 illustrate components that are common to each of first example needle module 1000 and second example needle module 1100.

As discussed in more detail herein, needle modules 100 according to the present disclosure are configured to be utilized for applying ink to skin of a subject, such as to apply a tattoo and/or permanent makeup to the skin of the subject. As schematically illustrated in FIGS. 1-8, a needle module 100 includes a module housing 110 and a needle assembly 140 operatively supported within the module housing. Module housing 110 extends along and defines a housing axis 102 and includes a housing tip 120 that defines a tip outlet 122. In particular, module housing 110 is configured such that housing axis 102 extends through housing tip 120 and/or tip outlet 122. In various examples, and as schematically illustrated in FIGS. 1-8, housing tip 120 may be described as being an end region and/or portion of housing tip 120. Accordingly, module housing 110 also may be described as terminating with, and/or as terminating at, housing tip 120.

As schematically illustrated in FIGS. 1-8, module housing 110 includes, or defines, an ink reservoir 112, such as may be configured to contain a volume of ink 50 to be applied to the skin of the subject. In particular, as used herein, ink reservoir 112 may include, be, and/or correspond to a volumetric region defined and/or enclosed by module housing 110 and/or housing tip 120 thereof that is occupied by ink 50 during operative use of needle module 100. As more specific examples, ink reservoir 112 may refer to a region defined and/or enclosed by module housing 110 and/or housing tip 120 into which ink 50 flows and/or settles, such as via gravity, capillary action, and/or surface tension, such that the ink within the ink reservoir is positioned to be delivered to the skin of the subject during operative use of needle module 100.

Ink 50 may include and/or be any of a variety of substances suitable for delivery to the subject's skin, examples of which include a fluid, a liquid, a pigment, a tattoo ink, a black tattoo ink, a colored (e.g., non-black) tattoo ink, and/or a permanent makeup ink. As used herein, needle module 100 also may be referred to as a needle cartridge 100, a tattoo cartridge 100, and/or a tattoo needle cartridge 100. Needle modules 100 according to the present disclosure may be utilized for applying ink 50 to skin of any of a variety of subjects, such as an animal, a human, and/or a living being with skin. In various examples, the subject may be a different individual than a user who operatively utilizes needle module 100 for applying ink 50, or the subject and the user may be the same individual.

As used herein, the term "axis," as used to describe and/or define a direction and/or a component of needle module 100, is intended to refer to a straight line that extends along the direction and/or along at least a portion of the component. Accordingly, in this manner, a direction may be uniquely defined and/or identified by a corresponding axis, and/or vice-versa. Additionally, in this manner, a description of a component as extending at least partially along an axis is intended to refer to a configuration in which at least a portion of the component extends along the axis and/or along the direction defined by the axis. In such descriptions, it is additionally within the scope of the present disclosure that another portion of the component may extend along a direction that is distinct from the direction corresponding to the stated axis. Stated differently, a description of a component as extending at least partially along an axis also encompasses examples in which a portion of the component extends along a direction that is non-parallel to the stated axis, that does not intersect the stated axis, that is angled relative to the stated axis, and/or that is not characterized by a well-defined axis.

Figure 5:
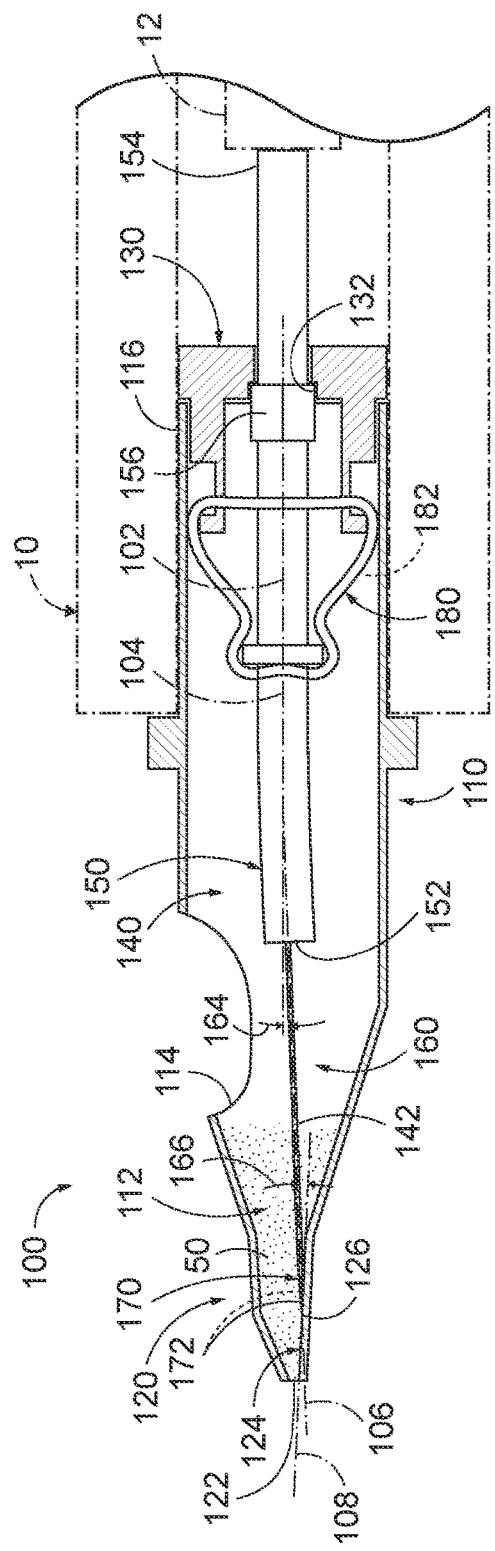
FIG. 5 is a schematic cross-sectional side elevation view representing examples of needle modules with a bent drive bar and with a needle assembly in a retracted position according to the present disclosure.
Figure 6:
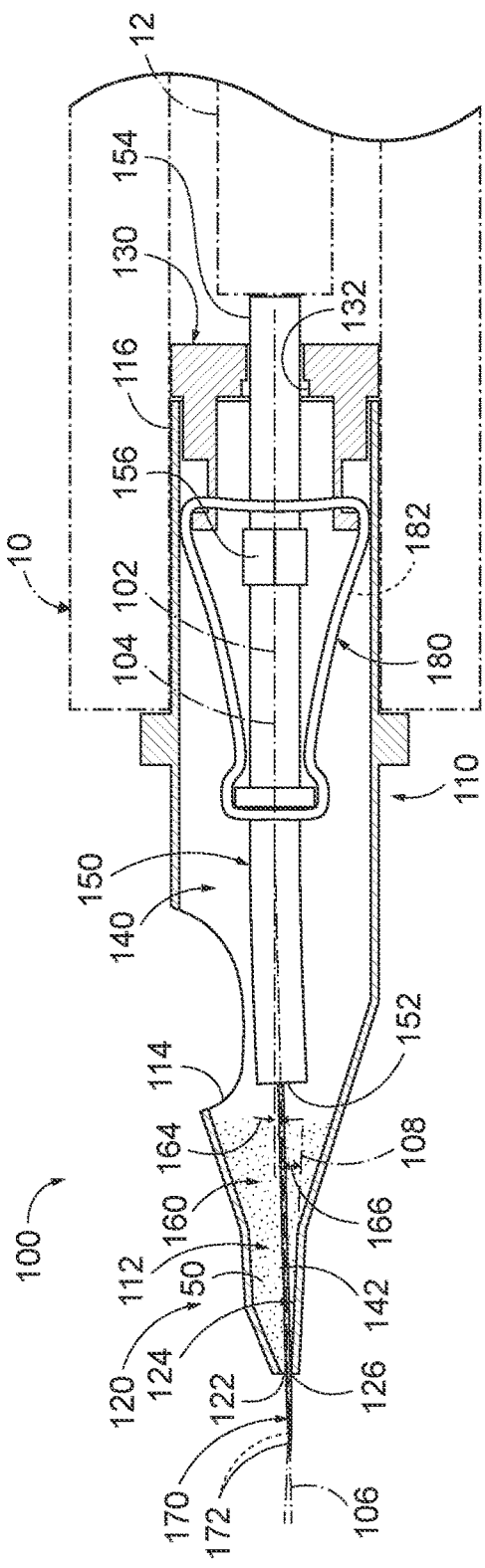
FIG. 6 is a schematic cross-sectional side elevation view representing the example needle modules of FIG. 5, with the needle assembly in an extended position according to the present disclosure.

In some examples, and as schematically illustrated in FIGS. 1-8, module housing 110 defines a reservoir opening 114 that permits access to ink reservoir 112, such as visual and/or fluid access to the ink reservoir. Reservoir opening 114 may assume and/or exhibit any of a variety of forms and/or shapes, examples of which include a hole, and aperture, a cutout, a channel, and/or a groove formed in module housing 110. In some examples, and as schematically illustrated in FIGS. 1-6 and less schematically illustrated in FIGS. 11-13, reservoir opening 114 is at least partially spaced apart from housing tip 120 and/or from tip outlet 122. In other examples, and as schematically illustrated in FIGS. 7-8 and less schematically illustrated in FIGS. 15-17, housing tip 120 includes and/or defines at least a portion of reservoir opening 114 such that reservoir opening 114 and tip outlet 122 are joined and/or continuous with one another. Stated differently, in such examples, reservoir opening 114 and tip outlet 122 may refer to respective portions or regions of a common cutout and/or aperture formed in module housing 110.

As schematically illustrated in FIGS. 1-8, needle assembly 140 of needle module 100 includes a drive bar 150 and a needle grouping 160 extending from the drive bar. More specifically, and as schematically illustrated in FIGS. 1-8, drive bar 150 extends at least partially along a drive bar axis 104, and needle grouping 160 extends from a needle grouping attachment end 152 of the drive bar and at least partially along a needle grouping axis 106. Stated differently, and as described in more detail herein, at least a portion of drive bar 150 extends along drive bar axis 104, and at least a portion of needle grouping 160 extends along needle grouping axis 106. As schematically illustrated in FIGS. 1-8, drive bar axis 104 may be at least substantially, and/or nominally fully, parallel to and/or collinear with housing axis 102. In this manner, drive bar 150 may be described as extending along a length of module housing 110.

As schematically illustrated in FIGS. 1-8, needle grouping 160 includes one or more needles 172. Needle assembly 140 is configured to reciprocate along drive bar axis 104 such that at least a portion of needle grouping 160 reciprocates into and out of module housing 110 via tip outlet 122. In particular, in some examples, needle assembly 140 is configured such that needle(s) 172 reciprocate into and out of module housing 110 via tip outlet 122 as needle assembly 140 reciprocates along drive bar axis 104. In this manner, the reciprocating motion of needle(s) 172 may operate to repeatedly puncture an upper layer of the subject's skin, thereby enabling needle module 100 to deposit ink 50 within the subject's skin. In various examples, and as schematically illustrated in FIGS. 1-8, needle(s) 172 may be described as being positioned at an end region and/or portion of needle grouping 160. Accordingly, needle grouping 160 also may be described as terminating with, and/or as terminating at, needle(s) 172.

As used herein, terms such as "reciprocating," "reciprocating motion," and the like, as used to describe the motion of a component along an axis and/or direction, are intended to refer to a motion in which the component repeatedly moves and/or translates back and forth along the axis and/or direction, such as in an oscillating manner. In the present disclosure, needle assembly 140 and/or a component thereof, such as needle grouping 160 and/or drive bar 150, may be described as reciprocating, translating, and/or moving into and/or out of module housing 110 when at least a portion of the needle assembly and/or of the component thereof enters and/or exits the module housing. In this manner, needle grouping 160 may be described as reciprocating into and out of module housing 110 even in examples and/or instances in which a portion of the needle grouping remains within the module housing during the reciprocating movement. Similarly, drive bar 150 may be described as reciprocating into and out of module housing 110 even in examples and/or instances in which a portion of the drive bar remains within the module housing during the reciprocating movement. As used herein, needle assembly 140 and/or any portion thereof may be described as reciprocating along drive bar axis 104 when the needle assembly and/or portion thereof moves, shifts, translates, etc. along a direction that is at least substantially parallel to the drive bar axis. However, such descriptions do not require that all portions and components of needle assembly 140 move in strict unison with one another, and it is within the scope of the present disclosure that a portion of needle assembly 140 may move along a direction that is not parallel to drive bar axis 104 as the needle assembly reciprocates along the drive bar axis.

As discussed in more detail herein, needle module 100 may be configured to facilitate a flow of ink 50 from ink reservoir 112 to needle(s) 172 via capillary action, such as may be enhanced via appropriate configuration of needle grouping 160 relative to module housing 110. In particular, needle modules 100 according to the present disclosure are configured such that needle grouping 160 contacts housing tip 120 at a needle grouping contact location 126 as the needle grouping reciprocates into and out of module housing 110. More specifically, in some examples, and as described in more detail herein, needle grouping 160 is angled relative to housing tip 120 at needle grouping contact location 126 at least when the needle grouping extends out of module housing 110. Such a configuration may enhance a flow of ink 50 from ink reservoir 112 to needle(s) 172 via capillary action as a result of enhanced adhesion between the ink and housing tip 120 at needle grouping contact location 126. In some examples, and as described in more detail herein, needle grouping contact location 126 is localized and/or limited in spatial extent in order to limit the extent to which the contact between needle grouping 160 and housing tip 120 restricts or hinders the flow of ink 50 through tip outlet 122. In various examples according to the present disclosure, needle module 100 is configured such that needle grouping 160 is brought into angled contact with needle grouping contact location 126 without the use or inclusion of structures that engage drive bar 150 and/or needle grouping 160 in order to urge the needle grouping into contact with housing tip 120. In particular, needle module 100 may be free from structures that engage drive bar 150 and/or needle grouping 160 to urge the needle grouping into angled contact with housing tip 120. Such structures may include structures that extend from, project from, and/or are operatively coupled to module housing 110 and that contact drive bar 150 and/or needle grouping 160 other than at needle grouping contact location 126 in a manner that biases the needle grouping toward the needle grouping contact location. Instead, and as described in more detail herein, needle modules 100 according to the present disclosure may be configured such that needle assembly 140 itself and/or a portion thereof is bent, curved, and/or angled in a manner that brings needle grouping 160 into contact with needle grouping contact location 126. Such a configuration also may operate to enhance a stability of needle grouping 160 and/or of needle(s) 172 relative to module housing 110. That is, configuring needle module 100 such that needle grouping 160 is biased into contact with needle grouping contact location 126 may operate to maintain needle(s) 172 at a consistent and predictable position relative to module housing 110 at least when the needle(s) are brought into contact with the subject's skin. Such a configuration thus may enable the user to more precisely control the position and/or motion of the needle(s) relative to the subject's skin.

As used herein, the term "angled," as used to refer to a configuration and/or orientation of a first component relative to a second component, is intended to refer to a configuration and/or orientation in which the first component and the second component do not extend fully, or nominally fully, parallel to one another or collinear with one another. For example, a first component may be described as being angled relative to a second component when the first component extends along a first direction and the second component extends along a second direction that deviates from the first direction, such as by at least 1 degree and/or by at most 90 degrees.

As schematically illustrated in FIGS. 1-8, needle assembly 140 is configured to translate relative to module housing 110 along a direction at least substantially parallel to drive bar axis 104 to transition the needle assembly among a plurality of positions defined between and including a retracted position and an extended position. In particular, when needle assembly 140 is in the retracted position, needle grouping 160 is maximally received within the module housing. When needle assembly 140 is in the extended position, needle(s) 172 extend maximally distal to housing tip 120. FIGS. 1, 3, 5, and 7 schematically illustrate examples in which needle assembly 140 is in the retracted position, while FIGS. 2, 4, 6, and 8 schematically illustrate examples in which the needle assembly is in the extended position. As used herein, superlative terms such as "maximal," "maximally," and the like refer to limits of corresponding ranges of extents, conditions, values, etc. that are exhibited during operative use of needle module 100. Thus, for example, needle grouping 160 may be described as being maximally received within module housing 110 when needle (s) 172 are received within the module housing and are spaced apart from tip outlet 122 by a maximum distance that is reached during a reciprocating cycle of needle assembly 140. While FIGS. 1-8 schematically represent examples in which needle assembly 140 is in the retracted position or in the extended position, the needle assembly 140 also may be operable to apply ink 50 to skin of the subject when the needle assembly is at an intermediate position among the plurality of positions defined between (and excluding) the retracted position and the extended position. As an example, during operative use of needle module 100, needle(s) 172 may penetrate the skin of the subject and/or deliver ink 50 to the skin of the subject while needle assembly 140 is at an intermediate position in which the needle(s) extend out of housing tip 120 by a distance less than that corresponding to the extended position.

When needle assembly 140 is in the retracted position, needle(s) 172 may be at least partially concealed, shielded, and/or protected by module housing 110 and/or housing tip 120. Stated differently, in such examples, when needle assembly 140 is in the retracted position, module housing 110 and/or housing tip 120 may restrict and/or prevent needle(s) 172 from inadvertent contact with objects exterior of the module housing. For example, and as schematically illustrated in FIGS. 1, 3, 5, and 7, when needle assembly 140 is in the retracted position, needle(s) 172 may be at least substantially and/or fully contained within module housing 110, and/or may not extend beyond housing tip 120.

As discussed, needle module 100 may be configured such that needle grouping 160 is angled relative to housing tip 120 at needle grouping contact location 126, such as at least when the needle grouping extends out of module housing 110. Stated differently, needle module 100 may be configured such that at least a portion of needle grouping 160 that contacts needle grouping contact location 126 extends along a direction that is angled relative to the portion of housing tip 120 that defines needle grouping contact location 126. More specifically, and as schematically illustrated in FIGS. 1-8, at least a portion of needle grouping 160 may extend along needle grouping axis 106 at needle grouping contact location 126. That is, in such examples, a portion and/or region of needle grouping 160 that contacts needle grouping contact location 126 extends along needle grouping axis 106. In this manner, in such examples, needle grouping axis 106 may intersect and/or extend tangentially to needle grouping contact location 126, or the needle grouping axis may extend through a portion and/or region of needle grouping 160 that is in contact with and/or immediately adjacent to the needle grouping contact location.

Needle grouping contact location 126 may refer to, include, and/or be any of a variety of regions of housing tip 120 that are contacted by needle(s) 172. In various examples, and as schematically illustrated in FIGS. 1-10, housing tip 120 defines a needle guide surface 124 that includes needle grouping contact location 126. In particular, and as schematically illustrated in FIGS. 1-10, needle guide surface 124 may be a surface of housing tip 120 that extends along a direction at least substantially parallel to housing axis 102. In some examples, as schematically illustrated in FIGS. 1-6 and 9 and as perhaps best seen in FIG. 9, needle guide surface 124 is curved along a direction perpendicular to housing axis 102. In particular, examples in which needle guide surface 124 is curved may correspond to examples in which needle module 100 is a liner module, as described herein. In other examples, as schematically illustrated in FIGS. 7-8 and 10 and as perhaps best seen in FIG. 10, needle guide surface 124 includes and/or is a flat surface. In particular, examples in which needle guide surface 124 is flat may correspond to examples in which needle module 100 is a shader module, as described herein.

Needle module 100 may be configured to transition needle assembly 140 between the retracted position and the extended position in any of a variety of manners, such as in response to an external force. More specifically, in some examples, and as schematically illustrated in FIGS. 1-8, needle module 100 may be configured to be utilized in conjunction with a reciprocating machine 10 with a machine drive member 12 that engages a reciprocating machine end 154 of drive bar 150 exterior of module housing 110. In such examples, reciprocating machine end 154 receives a driving force, such as a reciprocating force, from machine drive member 12 to reciprocate drive bar 150 relative to module housing 110. As schematically illustrated in FIGS. 1-8, reciprocating machine end 154 is opposite needle grouping attachment end 152. Reciprocating machine 10 may include and/or be any of a variety of machines and/or devices, such as a tattoo machine, a pen-style tattoo machine, a rotary tattoo machine, and/or a coil tattoo machine. In some examples, and as schematically illustrated in FIGS. 1-8, reciprocating machine 10 receives and engages a portion of module housing 110 during operative use of needle module 100. In such examples, reciprocating machine 10 may be described as engaging and supporting needle module 100 during operative use of the needle module. Accordingly, in some such examples, module housing 110 is configured and/or shaped to be at least partially received within reciprocating machine 10 during operative use of the needle module. As a more specific example, and as schematically illustrated in FIGS. 1-8 and less schematically illustrated in FIGS. 11-13 and 15-17, module housing 110 may be at least substantially cylindrical.

As used herein, phrases such as "in operative use," "during operative use," "operatively utilized," and the like generally refer to a configuration in which needle module 100 is operatively coupled to and supported by reciprocating machine 10 and is being utilized to deliver ink 50 to the subject's skin. However, such descriptions are not limiting, and it is additionally within the scope of the present disclosure that needle module 100, as described herein, is not always in operative use and/or utilized in conjunction with reciprocating machine 10 and/or ink 50. Stated differently, descriptions of features, characteristics, configurations, etc. of needle module 100 and/or any portion thereof that are presented with reference to needle module 100 in operative use may continue to describe and/or characterize the needle module and/or portion thereof even while the needle module is not in operative use and/or while the needle module is not actively exhibiting such characteristics.

Needle grouping 160 may assume any of a variety of forms and/or configurations, such as may correspond to an intended application of needle module 100. In some examples, and as schematically illustrated in FIGS. 1-8, needle grouping 160 may be described as including a needle head 170 and a needle bar 142. Needle head 170 includes needle(s) 172, and needle bar 142 is coupled to needle grouping attachment end 152 of drive bar 150. In this manner, in such examples, needle bar 142 may be operatively attached to and/or directly coupled to each of needle head 170 and drive bar 150. Accordingly, the needle bar may be described as operatively interconnecting the needle head and the drive bar. In some examples, at least a portion of needle head 170 is operatively coupled to needle bar 142, such as via soldering, welding, bonding, adhesive bonding, and/or via a mechanical fastener. Additionally or alternatively, needle bar 142 and at least a portion of needle head 170 may be monolithic, coextensive with one another, and/or integrally formed with one another. In such examples, needle bar 142 and needle head 170 may include and/or refer to respective components and/or regions of needle grouping 160.

Needle head 170 may include any of a variety of configurations of needle(s) 172, including any of a variety of numbers and/or patterns of needles, such as may correspond to an intended functionality and/or style of needle module 100. As examples, needle module 100 may be a liner module, a shader module, a round shader module, a flat shader module, a magnum shader module, and/or a hybrid module. In particular, in such examples, a liner module may be configured to apply ink 50 to the subject's skin along a linear path and/or in a dotted pattern, while a shader module may be configured to apply ink to the subject's skin across a two-dimensional area of the subject's skin. However, this is not required, and it is additionally within the scope of the present disclosure that a liner module may be configured and/or utilized to apply ink 50 across a two-dimensional area of the subject's skin, and/or that a shader module may be configured and/or utilized to apply ink to the subject's skin along a linear path. As additional examples, needle grouping 160 and/or needle head 170 may include 1 needle 172, at least 2 needles 172, at least 5 needles 172, at least 10 needles 172, at least 15 needles 172, at least 20 needles 172, at least 25 needles 172, at least 30 needles 172, at most 35 needles 172, at most 27 needles 172, at most 22 needles 172, at most 17 needles 172, at most 12 needles 172, at most 7 needles 172, and/or at most 3 needles 172. In some examples, it may be desirable to configure a liner module to include a relatively small number of needles 172 (e.g., fewer than 15 needles, fewer than 10 needles, and/or fewer than 5 needles) in order to apply ink 50 to the subject's skin in a finely detailed pattern. In other examples, it may be desirable to configure a shader module to include a relatively large number of needles 172 (e.g., more than 10 needles, more than 15 needles, and/or more than 20 needles) in order to apply ink 50 to the subject's skin across a large two-dimensional area relatively quickly.

In some examples, needle grouping 160 and/or needle head 170 includes a plurality of needles arranged in a circularly clustered configuration. As a more specific example, FIGS. 11-14 illustrate a first example needle module 1000 that includes a plurality of needles 172 (visible in FIGS. 12-14) arranged in a circularly clustered configuration. In such examples, needle module 100 may be referred to as a liner module 100 that is configured to apply ink 50 to skin along a linear path. Additionally, the schematic illustrations of FIGS. 1-6 and 9 correspond to examples in which needle module 100 is a liner module.

In other examples, needle grouping 160 and/or needle head 170 includes a plurality of needles arranged in a linear configuration. In some such examples, and as schematically illustrated in FIGS. 7-8, needle grouping 160 and/or needle head 170 includes a first needle subset 174 and a second needle subset 176, each of which includes a respective plurality of needles 172 arranged in a linear configuration. As a more specific example, FIGS. 15-19 illustrate a second example needle module 1100 that includes first needle subset 174 and second needle subset 176 (best seen in FIGS. 17-19) including respective pluralities of needles 172. In such examples, needle module 100 may be referred to as a shader module 100 that is configured to apply ink to skin across a two-dimensional area. Additionally, the schematic illustrations of FIGS. 7-8 and 10 correspond to examples in which needle module 100 is a shader module.

Figure 17:
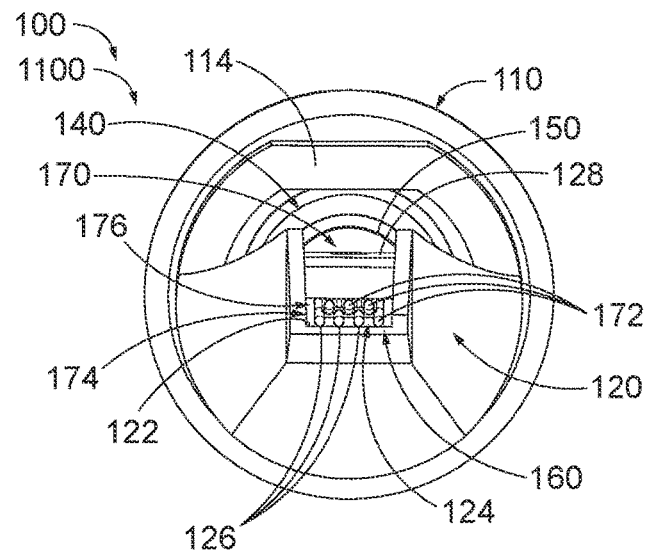
FIG. 17 is a front elevation view of the second example needle module of FIGS. 15-16, with the needle assembly in the retracted position.
Figure 18:
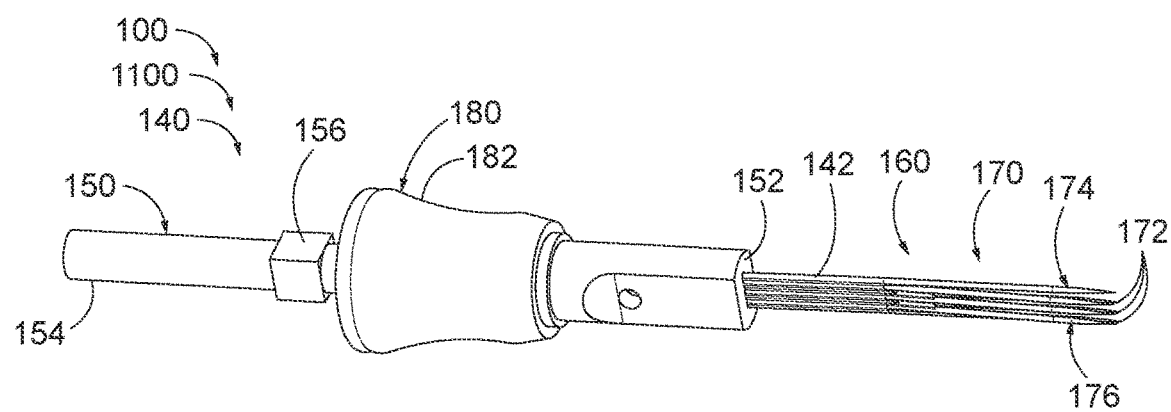
FIG. 18 is a top side perspective view of the needle assembly of the second example needle module of FIGS. 15-17.
Figure 19:
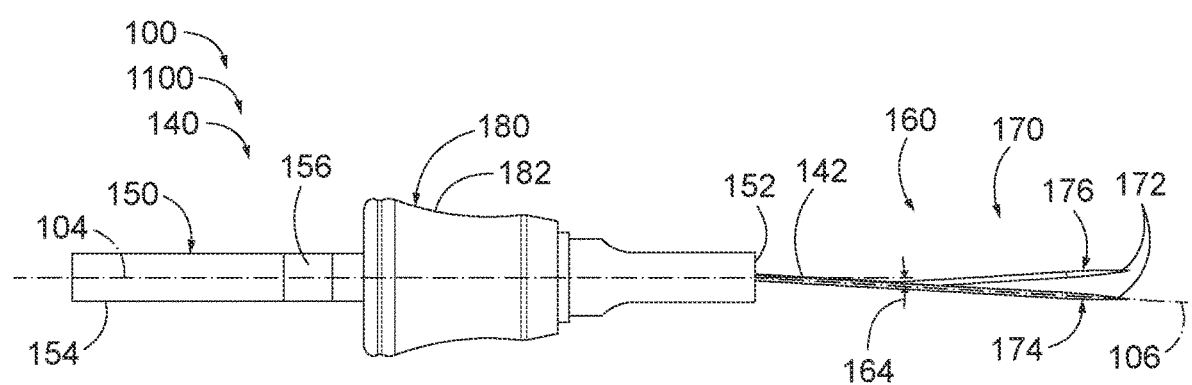
FIG. 19 is a side elevation view of the needle assembly of the second example needle module of FIGS. 15-18.

In some examples, and as illustrated in FIGS. 15-19 and perhaps best shown in FIGS. 17-19, each needle 172 of first needle subset 174 extends nominally fully parallel to each other needle of the first needle subset, and each needle 172 of second needle subset 176 extends nominally fully parallel to each other needle of the second needle subset. In some more specific examples, each needle 172 of first needle subset 174 extends nominally fully parallel to each needle of second needle subset 176. In some examples, each needle 172 of first needle subset 174 extends nominally fully parallel to needle bar 142 and/or to another component and/or region of needle grouping 160.

In some examples, and as schematically illustrated in FIGS. 7-8, each needle 172 of first needle subset 174 contacts needle grouping contact location 126. In some examples in which needle grouping 160 includes first needle subset 174 and second needle subset 176, each needle 172 the second needle subset also may be configured to contact a portion of module housing 110. In particular, in some examples, and as schematically illustrated in FIGS. 7-8 and less schematically illustrated in FIGS. 15-17, housing tip 120 includes a needle retainer 128 that faces needle guide surface 124, and each needle 172 of second needle subset 176 contacts the needle retainer. In some such examples, needle retainer 128 may be described as extending within reservoir opening 114. In some examples, first needle subset 174 and second needle subset 176 are biased apart from one another such that, as needle assembly 140 reciprocates relative to module housing 110, each needle of the first needle subset is continually urged into contact with needle guide surface 124 and each needle of the second needle subset is continually urged into contact with the needle retainer. In some such examples, needle module 100 also may be referred to as a magnum module 100 and/or as a magnum shader module 100.

FIGS. 9-10 schematically illustrate examples of configurations of needle grouping contact location 126 upon needle guide surface 124. FIGS. 9-10 may be described as corresponding to the schematic representations of FIGS. 1-8, with FIG. 9 corresponding to the examples of FIGS. 1-6 and with FIG. 10 corresponding to the examples of FIGS. 7-8. The representations of needle grouping contact location 126 illustrated in solid lines in FIGS. 9-10 generally correspond to examples and/or instances in which needle assembly 140 is in the retracted position (as schematically illustrated in FIGS. 1, 3, 5, and 7). The representations of needle grouping contact location 126 illustrated in dashed lines in FIGS. 9-10 generally correspond to examples and/or instances in which needle assembly 140 is in the extended position (as schematically illustrated in FIGS. 2, 4, 6, and 8). In this manner, FIGS. 9-10 may be described as illustrating manners in which needle grouping contact location 126 may shift relative to needle guide surface 124 during operative use of needle module 100.

In some examples, and as schematically illustrated in FIG. 9, needle grouping contact location 126 is a single point of contact, and/or represents a single region of contact. For example, needle grouping contact location 126 may include and/or be a region of contact that extends along a direction at least substantially perpendicular to needle grouping axis 106 and/or along a direction at least substantially parallel to the needle grouping axis. FIG. 9 may be described as schematically representing examples in which needle grouping 160 (schematically illustrated in FIGS. 1-6) includes a single needle 172, or examples in which only one needle 172 of needle grouping 160 (schematically illustrated in FIGS. 1-6) contacts housing tip 120. More specifically, FIG. 9 may be described as representing examples in which needle module 100 is a liner module.

In other examples, and as schematically illustrated in FIG. 10, needle grouping contact location 126 refers to a discrete plurality of spaced-apart contact locations and/or regions, such as a plurality of spaced-apart single points of contact and/or a plurality of spaced-apart discrete regions of contact. In this manner, FIG. 10 may be described as schematically representing examples in which needle grouping 160 includes a plurality of needles 172 (schematically illustrated in FIGS. 7-8) that are in contact with housing tip 120. More specifically, FIG. 10 may be described as representing examples in which needle module 100 is a shader module.

FIGS. 9-10 also schematically represent a manner in which needle grouping contact location 126 may shift relative to housing tip 120 as needle assembly 140 reciprocates into and out of module housing 110. In particular, and as schematically illustrated in FIGS. 9-10, needle module 100 may be configured such that needle grouping contact location 126 shifts relative to module housing 110 along a direction at least substantially parallel to drive bar axis 104 as needle assembly 140 reciprocates into and out of module housing 110, between the location(s) illustrated in solid lines and the location(s) illustrated in dashed lines.

In various examples according to the present disclosure, needle grouping 160 is continuously and positively biased against needle guide surface 124 and/or needle grouping contact location 126 while needle assembly 140 reciprocates into and out of module housing 110. In this manner, as used herein, the term "contact location" is intended to refer to a location, a point, and/or a region at which needle(s) 172 contact housing tip 120 at a particular moment and/or instant in time. Accordingly, descriptions herein of needle grouping contact location 126 being a single point and/or a localized region are not intended to imply that the point and/or region is fixed relative to housing tip 120 at all times during operative use of needle module 100. Instead, such descriptions refer to the characteristic that needle grouping contact location 126 is limited in spatial extent at a given moment in time. As more specific examples, and as schematically illustrated in FIGS. 9-10, needle grouping contact location 126 may have a contact location longitudinal extent 127, and needle guide surface 124 may have a guide surface longitudinal extent 125 such that the contact location longitudinal extent is at most 10% of the guide surface longitudinal extent, at most 5% of the guide surface longitudinal extent, and/or at most 1% of the guide surface longitudinal extent. As schematically illustrated in FIGS. 9-10, each of guide surface longitudinal extent 125 and contact surface longitudinal extent 127 may be measured along needle guide surface 124 and in a direction at least substantially parallel to housing axis 102.

Moreover, it is additionally within the scope of the present disclosure that needle grouping contact location 126 is nominally fully stationary relative to module housing 110 while needle assembly 140 reciprocates relative to the module housing, such as while at least a portion of needle grouping 160 extends out of the module housing. For example, needle module 100 may be configured such that needle grouping contact location 126 remains at a portion of needle guide surface 124 immediately adjacent to tip outlet 122 when needle grouping 160 extends out of module housing 110.

Needle module 100 may have any of a variety of features and/or configurations such that needle(s) 172 contact needle guide surface 124 at needle grouping contact location 126 as described herein. In particular, as described herein, needle grouping 160 may be angled relative to housing tip 120 such that the needle grouping contacts the housing tip at the needle grouping contact location. As a more specific example, and as schematically illustrated in FIGS. 1-10, the angled configuration of needle grouping 160 may be described in terms of a contact location tangent plane 108 defined by housing tip 120. In particular, and as schematically illustrated in FIGS. 1-10, contact location tangent plane 108 may extend tangentially to housing tip 120 and/or to needle guide surface 124 thereof at least at needle grouping contact location 126. Stated differently, in such examples, contact location tangent plane 108 is a plane that is tangent to housing tip 120 at the location that needle grouping 160 contacts the housing tip. In some examples, such as in the examples schematically illustrated in FIGS. 7-8 and 10, needle guide surface 124 includes a flat surface that extends within contact location tangent plane 108. In this manner, contact location tangent plane 108 may be nominally fully parallel to and/or coplanar with needle guide surface 124. In other examples, such as in the examples schematically illustrated in FIGS. 1-6 and 9, needle guide surface 124 includes a curved surface that intersects contact location tangent plane 108 in a line, such as a line along which needle grouping contact location 126 moves as needle assembly 140 reciprocates relative to module housing 110. In some examples, such as in the examples schematically illustrated in FIGS. 1-8, contact location tangent plane 108 may be angled relative to housing axis 102 such that the contact location tangent plane intersects the housing axis. However, this is not required of all examples of needle module 100, and it is additionally within the scope of the present disclosure that the contact location tangent plane may be nominally fully parallel to the housing axis. As more specific examples, the housing axis may extend within the contact location tangent plane, or the housing axis and the contact location tangent plane may be non-intersecting.

As schematically illustrated in FIGS. 1-8, a configuration of needle grouping 160 relative to housing tip 120 may be described in terms of a housing contact angle 166, as measured between needle grouping axis 106 and contact location tangent plane 108. As examples, housing contact angle 166 may be at least 1 degree, at least 2 degrees, at least 3 degrees, at least 5 degrees, at most 10 degrees, at most 7 degrees, at most 5 degrees, at most 4 degrees, at most 2.5 degrees, and/or at most 1.5 degrees.

Figure 2:
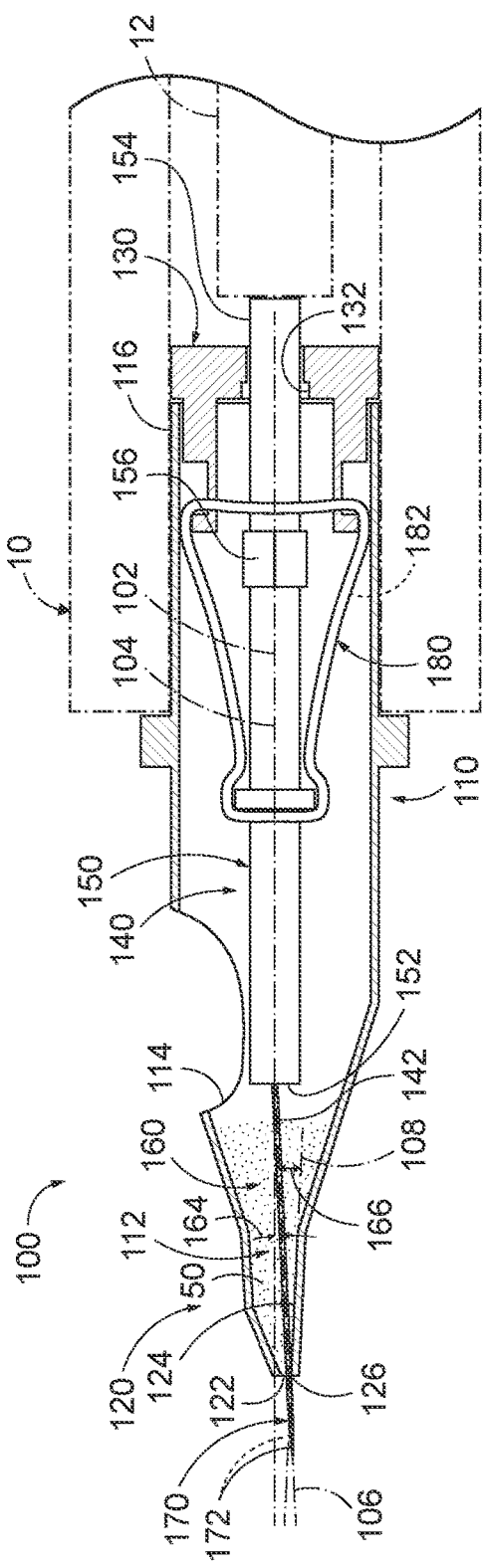
FIG. 2 is a schematic cross-sectional side elevation view representing the example needle modules of FIG. 1, with the needle assembly in an extended position according to the present disclosure.

Needle grouping 160 and/or module housing 110 may have exhibit any of a variety of configurations to yield housing contact angle 166 as described herein. In some examples, and as schematically illustrated in FIGS. 1-2, needle grouping 160 is operatively coupled to drive bar 150 such that needle grouping axis 106 deviates from drive bar axis 104 by a needle grouping bias angle 164, as measured between the needle grouping axis and the drive bar axis. As more specific examples, needle grouping bias angle 164 may be at least 1 degree, at least 2 degrees, at least 3 degrees, at least 5 degrees, at most 10 degrees, at most 7 degrees, at most 5 degrees, at most 4 degrees, at most 2.5 degrees, and/or at most 1.5 degrees. Stated differently, in such examples, drive bar 150 and needle grouping 160 each may be at least substantially straight along all, or nearly all, of a respective length thereof, and the needle grouping may be joined to the drive bar such that the needle grouping extends from the drive bar at an angle relative to drive bar axis 104. Stated another way, needle grouping 160 may be joined to drive bar 150 at needle grouping attachment end 152 such that the needle grouping extends away from the needle grouping attachment end along a direction that is angled relative to a direction along which the drive bar extends at the needle grouping attachment end. In this manner, in such examples, and as schematically illustrated in FIGS. 1-2, needle grouping 160 may extend along needle grouping axis 106 from drive bar 150 to needle(s) 172.

FIGS. 7-8 and 15-19 also may be described as schematically illustrating examples in which needle grouping 160 extends from drive bar 150 at an angle. In particular, FIGS. 7-8 and 19 illustrate configurations in which needle grouping 160 extends along needle grouping axis 106 from drive bar 150 to needles 172 of first needle subset 174 and in which the needle grouping axis is angled relative to drive bar axis 104 by needle grouping bias angle 164. In the examples of FIGS. 7-8 and 15-19, and as best illustrated in FIGS. 7-8 and 19, second needle subset 176 is operatively coupled to a remainder of needle grouping 160 such that the second needle subset extends along a direction that is angled relative to needle grouping axis 106.

Figure 3:
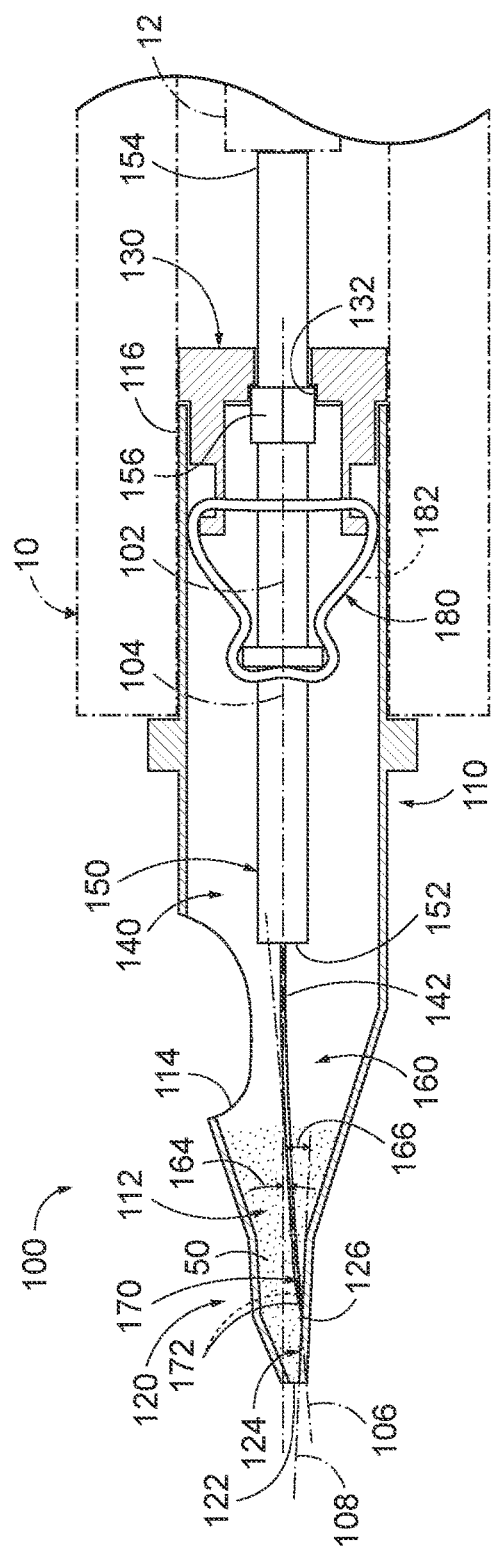
FIG. 3 is a schematic cross-sectional side elevation view representing examples of needle modules with a bent needle grouping and with a needle assembly in a retracted position according to the present disclosure.
Figure 4:
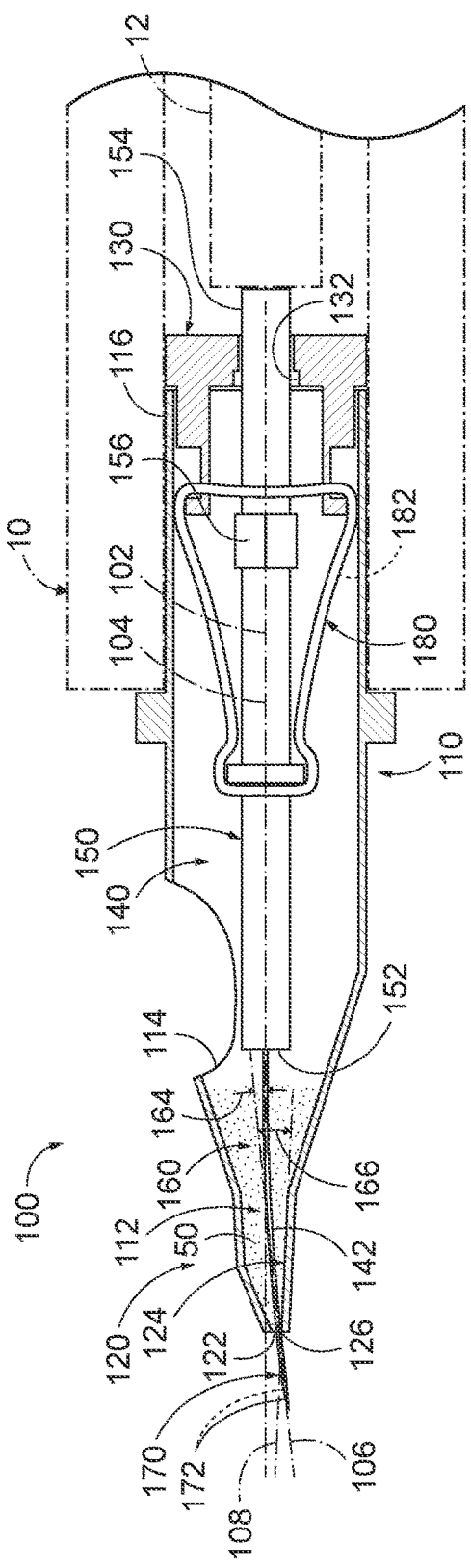
FIG. 4 is a schematic cross-sectional side elevation view representing the example needle modules of FIG. 3, with the needle assembly in an extended position according to the present disclosure.

Additionally or alternatively, in some examples, and as schematically illustrated in FIGS. 3-4, needle grouping 160 may be bent and/or curved at a location between drive bar 150 and needle(s) 172 about an axis that is perpendicular to needle grouping axis 106. In particular, FIGS. 3-4 schematically illustrate an example in which needle grouping 160 is coupled to drive bar 150 such that the needle grouping extends nominally fully parallel to the drive bar at locations proximate to needle grouping attachment end 152 of the drive bar, and in which the needle grouping is arced such that needle grouping axis 106 is angled relative to each of drive bar axis 104 and contact location tangent plane 108.

Additionally or alternatively, in some examples, and as schematically illustrated in FIGS. 5-6, drive bar 150 may be bent and/or curved at a location between needle grouping 160 and reciprocating machine end 154 about an axis that is perpendicular to drive bar axis 104. In such examples, and as schematically illustrated in FIGS. 5-6, needle grouping 160 may extend along needle grouping axis 106 from needle grouping attachment end 152 of drive bar 150 to needle head 170, and the drive bar itself may be bent, curved, arced, etc. such that the needle grouping axis is angled relative to drive bar axis 104 by needle grouping bias angle 164. Stated differently, in such examples, and as schematically illustrated in FIGS. 5-6, drive bar 150 may be bent, curved, arced, etc. such that a portion of the drive bar at needle grouping attachment end 152 extends along a direction that is angled relative to a direction along which a portion of the drive bar at reciprocating machine end 154 extends. As a more specific example, and as schematically illustrated in FIGS. 5-6, a portion of drive bar 150 at reciprocating machine end 154 may extend along drive bar axis 104, while a portion of the drive bar at needle grouping attachment end 152 may extend along an axis that is angled relative to the drive bar axis, such as needle grouping axis 106.

While FIGS. 1-8 schematically illustrate various examples of distinct configurations that may yield needle grouping bias angle 164, it is within the scope of the present disclosure that any features, configurations, and/or attributes illustrated and/or discussed in conjunction with any of FIGS. 1-8 also may be utilized in combination with any other features, configurations, and/or attributes illustrated and/or discussed in conjunction with any of FIGS. 1-8. For example, in various examples according to the present disclosure, drive bar 150 and needle grouping 160 each may be bent or curved. Additionally, while the present disclosure generally relates to examples in which needle grouping axis 106 is angled relative to drive bar axis 104, this is not required, and it is additionally within the scope of the present disclosure that the needle grouping axis may be nominally fully parallel to, and/or collinear with, the drive bar axis. In particular, in such examples, drive bar 150 and needle grouping 160 each may be nominally fully straight and may extend along a common axis (such as drive bar axis 104), and module housing 110 may be configured such that housing tip 120 meets and/or intersects the drive bar axis to yield needle grouping contact location 126 as described herein.

In various examples, and as described herein, needle assembly 140 must be maintained in a specific rotational orientation (e.g., with a specific rotational orientation with respect to housing axis 102) to ensure that needle grouping 160 operatively contacts housing tip 120 at needle grouping contact location 126. Accordingly, in some examples, needle module 100 includes one or more components for establishing and/or maintaining the rotational orientation of needle assembly 140 relative to module housing 110. In some examples, and as schematically illustrated in FIGS. 1-8 and less schematically illustrated in FIGS. 11-12 and 15-16, module housing 110 may include a drive end 116 opposite housing tip 120 such that drive bar 150 extends at least partially out of the drive end, and needle module 100 additionally may include a housing cap 130 that is operatively coupled to the drive end. In some such examples, and as schematically illustrated in FIGS. 1,3,5, and 7, housing cap 130 may be configured to engage drive bar 150 at least when needle assembly 140 is in the retracted position. In some such examples, and as schematically illustrated in FIGS. 1-8 and less schematically illustrated in FIGS. 21-22, housing cap 130 includes a drive bar receiver 132 that receives and engages drive bar 150 at least when the needle assembly is in the retracted position. More specifically, in some such examples, and as schematically illustrated in FIGS. 1-8 and less schematically illustrated in FIGS. 14 and 18-20, drive bar 150 includes a drive bar locator 156 such that drive bar receiver 132 (shown in FIGS. 1-8) engages the drive bar locator to maintain the drive bar in a nominal drive bar orientation. In particular, when the drive bar is in the nominal drive bar orientation, drive bar axis 104 is nominally fully parallel to housing axis 102 at least when needle assembly 140 is in the retracted position. Additionally or alternatively, when the drive bar is in the nominal drive bar orientation, the drive bar assumes an angular orientation relative to the housing axis such that needle grouping 160 contacts needle guide surface 124 at least when the needle assembly is in the retracted position.

In some examples, drive bar receiver 132 and drive bar locator 156 have shapes that are corresponding and/or mating such that engagement between the drive bar receiver and the drive bar locator restricts rotation of drive bar 150 relative to housing cap 130 (and hence relative to module housing 110). In particular, in some examples, drive bar locator 156 may have a cross-sectional shape, as viewed in a plane perpendicular to drive bar axis 104, that is the same as at least a portion of a cross-sectional shape of drive bar receiver 132. As more specific examples, drive bar locator 156 and/or drive bar receiver 132 each may have cross-sectional shapes that are triangular, rectangular, square, at least partially flat, and/or non-circular. In particular, FIG. 20 illustrates an example in which drive bar locator 156 has a cross-sectional shape that is square, while FIGS. 21-22 illustrate an example in which drive bar receiver 132 has a cross-sectional shape that includes square components (e.g., corners) superimposed on a circle for receiving drive bar 150 extending therethrough.

In some examples, needle assembly 140 is biased toward the retracted position. More specifically, in some such examples, and as schematically illustrated in FIGS. 1-8 and less schematically illustrated in FIGS. 14 and 18-19, needle module 100 includes a biasing member 180 that biases needle assembly 140 toward the retracted position. In some such examples, biasing member 180 is an elastic biasing member that is operatively coupled to each of housing cap 130 and needle assembly 140 and that resiliently deforms as needle assembly 140 reciprocates between the retracted position and the extended positon. As a more specific example, biasing member 180 may include and/or be a diaphragm 182 that is operatively coupled to each of housing cap 130 and needle assembly 140. In such examples, diaphragm 182 also may operate to fluidly separate ink reservoir 112 from the housing cap, such as to shield reciprocating machine 10 and/or machine drive member 12 from ink 50 and/or from bodily fluids that may enter ink reservoir 112 during operative use of needle module 100. In some examples, biasing member 180 and/or diaphragm 182 also may exhibit a torsional resilience that operates to maintain drive bar 150 in a rotational orientation corresponding to the nominal drive bar orientation even when drive bar locator 156 is removed from drive bar receiver 132. When present, biasing member 180 generally does not exert a force upon needle assembly 140 other than a linear force along housing axis 102 and/or a torsional force about the housing axis. Stated differently, when present, biasing member 180 generally does not contribute to a tendency and/or a bias of needle grouping 160 toward engagement with needle grouping contact location 126.

Figure 23:
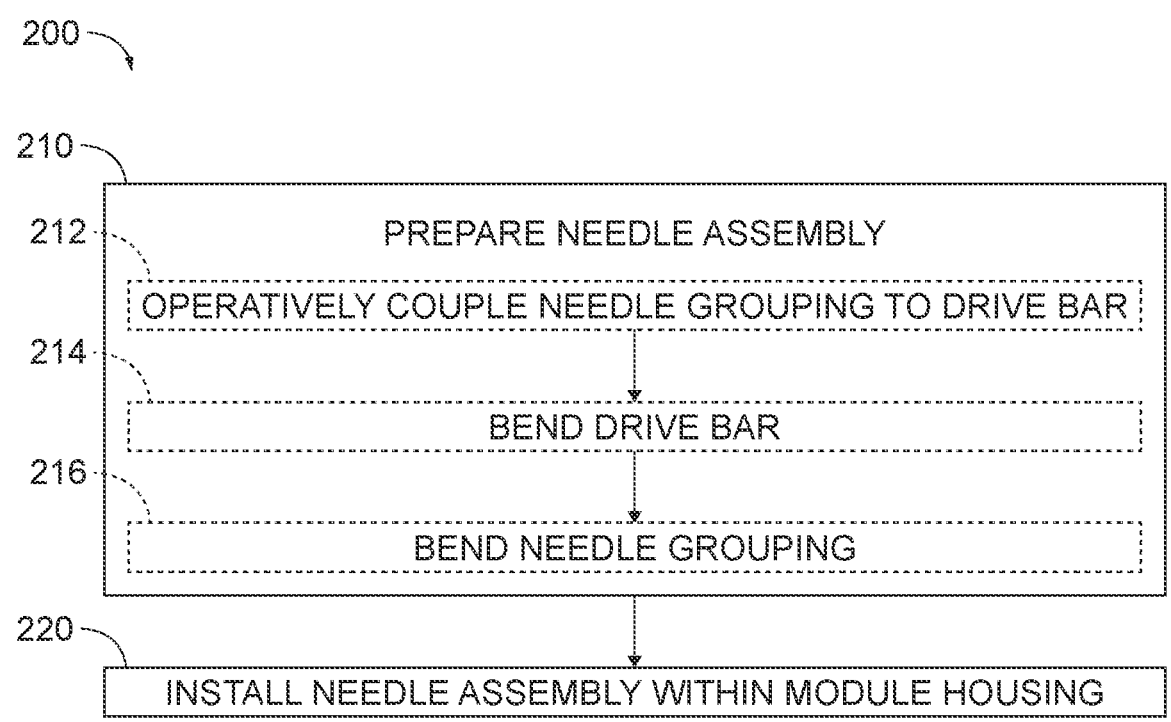
FIG. 23 is a flowchart representing examples of methods, according to the present disclosure, of assembling a needle module.

FIG. 23 is a flowchart representing examples of methods 200, according to the present disclosure, of assembling a needle module such as needle module 100, first example needle module 1000, and/or second example needle module 1100. As shown in FIG. 23, methods 200 include preparing, at 210, a needle assembly that includes a needle grouping operatively coupled to a drive bar and installing, at 220, the needle assembly within a module housing. Specifically, the installing the needle assembly within the module housing at 220 includes installing such that at least a portion of the needle grouping is configured to reciprocate into and out of the module housing and such that the needle grouping contacts the module housing at a needle grouping contact location as the needle grouping reciprocates into and out of the module housing. In various examples of methods 200, the preparing the needle assembly at 210 is performed prior to the installing the needle assembly within the module housing at 220. Examples of needle assemblies, drive bars, and/or needle groupings that may be utilized in conjunction with methods 200 are described herein with reference to needle assembly 140, drive bar 150, and/or needle grouping 160, respectively. Examples of module housings and/or needle grouping contact locations that may pertain to and/or be utilized in conjunction with methods 200 are described herein with reference to module housing 110 and/or needle grouping contact location 126, respectively.

The preparing the needle assembly at 210 may include preparing in any of a variety of manners. In some examples, and a shown in FIG. 23, the preparing the needle assembly at 210 includes operatively coupling, at 212, the needle grouping to the drive bar. As more specific examples, the operatively coupling the needle grouping to the drive bar at 212 may include inserting the needle grouping into the drive bar, molding the drive bar over the needle grouping, soldering the needle grouping to the drive bar, and/or otherwise operatively affixing the needle grouping to the drive bar.

In various examples, the preparing the needle assembly at 210 includes preparing such that at least a portion of the needle grouping extends along a needle grouping axis and such that at least a portion of the drive bar extends along a drive bar axis, with the needle grouping axis deviating from the drive bar axis by a needle grouping bias angle measured between the needle grouping axis and the drive bar axis. As more specific examples, the preparing the needle assembly at 210 may include configuring the needle assembly such that the needle grouping bias angle is at least 1 degree, at least 2 degrees, at least 3 degrees, at least 5 degrees, at most 10 degrees, at most 7 degrees, at most 5 degrees, at most 4 degrees, at most 2.5 degrees, and/or at most 1.5 degrees. Examples of needle grouping axes, drive bar axes, and/or needle grouping bias angles that may pertain to methods 200 are described herein with reference to needle grouping axis 106, drive bar axis 104, and/or needle grouping bias angle 164, respectively.

The preparing the needle assembly at 210 may include any of a variety of steps corresponding to and/or resulting in the needle grouping being characterized by the needle grouping bias angle. For example, the operatively coupling the needle grouping to the drive bar at 212 may include coupling such that the needle grouping extends away from a needle grouping attachment end of the drive bar (such as needle grouping attachment end 152 of drive bar 150) along a direction that is angled relative to a portion of the drive bar adjacent to the needle grouping attachment end. Additionally or alternatively, and as shown in FIG. 23, the preparing the needle assembly at 210 may include bending, at 214, the drive bar such that a portion of the drive bar extends along a direction that is curved and/or angled relative to the drive bar axis. Similarly, and as shown in FIG. 23, the preparing the needle assembly at 210 additionally or alternatively may include bending, at 216, the needle grouping such that a portion of the needle grouping extends along a direction that is curved and/or angled relative to the needle grouping axis. In such examples, the operatively coupling the needle grouping to the drive bar at 212, the bending the drive bar at 214, and/or the bending the needle grouping at 216 may be performed in any of a variety of sequences. As examples, the bending the drive bar at 214 may be performed prior to or subsequent to the operatively coupling the needle grouping to the drive bar at 212. Similarly, the bending the needle grouping at 216 may be performed prior to or subsequent to the operatively coupling the needle grouping to the drive bar at 212.

In the present disclosure, several of the examples have been discussed and/or presented in the context of flow diagrams, or flow charts, in which the methods are shown and described as a series of blocks, or steps. Unless specifically set forth in the accompanying description, it is within the scope of the present disclosure that the order of the blocks may vary from the illustrated order in the flow diagram, including with two or more of the blocks (or steps) occurring in a different order and/or concurrently. It also is within the scope of the present disclosure that the blocks, or steps, may be implemented as logic, which also may be described as implementing the blocks, or steps, as logics. In some applications, the blocks, or steps, may represent expressions and/or actions to be performed by functionally equivalent circuits or other logic devices. The illustrated blocks may, but are not required to, represent executable instructions that cause a computer, processor, and/or other logic device to respond, to perform an action, to change states, to generate an output or display, and/or to make decisions.

As used herein, the term "and/or" placed between a first entity and a second entity means one of (1) the first entity, (2) the second entity, and (3) the first entity and the second entity. Multiple entities listed with "and/or" should be construed in the same manner, i.e., "one or more" of the entities so conjoined. Other entities may optionally be present other than the entities specifically identified by the "and/or" clause, whether related or unrelated to those entities specifically identified. Thus, as a non-limiting example, a reference to "A and/or B," when used in conjunction with open-ended language such as "comprising," may refer, in one embodiment, to A only (optionally including entities other than B); in another embodiment, to B only (optionally including entities other than A); in yet another embodiment, to both A and B (optionally including other entities). These entities may refer to elements, actions, structures, steps, operations, values, and the like.

As used herein, the phrase "at least one," in reference to a list of one or more entities, should be understood to mean at least one entity selected from any one or more of the entity in the list of entities, but not necessarily including at least one of each and every entity specifically listed within the list of entities and not excluding any combinations of entities in the list of entities. This definition also allows that entities may optionally be present other than the entities specifically identified within the list of entities to which the phrase "at least one" refers, whether related or unrelated to those entities specifically identified. Thus, as a non-limiting example, "at least one of A and B" (or, equivalently, "At least one of A or B," or, equivalently, "at least one of A and/or B") may refer, in one embodiment to at least one, optionally including more than one, A, with no B present (and optionally including entities other than B); in another embodiment, to at least one, optionally including more than one, B, with no A present (and optionally including entities other than A); in yet another embodiment, to at least one, optionally including more than one, A, and at least one, optionally including more than one, B (and optionally including other entities). In other words, the phrases "at least one," "one or more," and "and/or" are open-ended expressions that are both conjunctive and disjunctive in operation.

For example, each of the expressions "at least one of A, B, and C," "at least one of A, B, or C," "one or more of A, B, and C," "one or more of A, B, or C," and "A, B, and/or C" may mean A alone, B alone, C alone, A and B together, A and C together, B and C together, A, B, and C together, and optionally any of the above in combination with at least one other entity.

As used herein, the phrase "at least substantially," when modifying a degree or relationship, includes not only the recited "substantial" degree or relationship, but also the full extent of the recited degree or relationship. A substantial amount of a recited degree or relationship may include at least 75% of the recited degree or relationship. For example, a first direction that is at least substantially parallel to a second direction includes a first direction that is within an angular deviation of 22.5° relative to the second direction and also includes a first direction that is identical to the second direction.

As used herein, the phrase "nominally fully," when modifying a degree or relationship, includes the full extent of the recited degree or relationship as well as degrees or relationships that differ from the full extent of the recited degree or relationship by up to 1%. For example, a first direction that is nominally fully parallel to a second direction includes a first direction that is within an angular deviation of 0.9° relative to the second direction and also includes a first direction that is identical to the second direction. In this manner, the phrase "nominally fully" may be substituted in place of the phrase "at least substantially." Stated differently, as used herein, the phrase "at least substantially" is intended to encompass degrees or relationships that are described with the phrase "nominally fully."

As used herein, the terms "adapted" and "configured" mean that the element, component, or other subject matter is designed and/or intended to perform a given function. Thus, the use of the terms "adapted" and "configured" should not be construed to mean that a given element, component, or other subject matter is simply "capable of" performing a given function but that the element, component, and/or other subject matter is specifically selected, created, implemented, utilized, programmed, and/or designed for the purpose of performing the function. It also is within the scope of the present disclosure that elements, components, and/or other recited subject matter that is recited as being adapted to perform a particular function may additionally or alternatively be described as being configured to perform that function, and vice versa.

As used herein, the terms "selective" and "selectively," when modifying an action, movement, configuration, or other activity of one or more components or characteristics of an apparatus, mean that the specific action, movement, configuration, or other activity is a direct or indirect result of one or more dynamic processes, as described herein. The terms "selective" and "selectively" thus may characterize an activity that is a direct or indirect result of user manipulation of an aspect of, or one or more components of, the apparatus, or may characterize a process that occurs automatically, such as via the mechanisms disclosed herein.

As used herein, the phrase "for example," the phrase "as an example," and/or simply the term "example," when used with reference to one or more components, features, details, structures, embodiments, and/or methods according to the present disclosure, are intended to convey that the described component, feature, detail, structure, embodiment, and/or method is an example of components, features, details, structures, embodiments, and/or methods according to the present disclosure. Thus, the described component, feature, detail, structure, embodiment, and/or method is not intended to be limiting, required, or exclusive/exhaustive; and other components, features, details, structures, embodiments, and/or methods, including structurally and/or functionally similar and/or equivalent components, features, details, structures, embodiments, and/or methods, are also within the scope of the present disclosure.

Examples of needle modules and methods according to the present disclosure are presented in the following enumerated paragraphs. It is within the scope of the present disclosure that an individual step of a method recited herein, including in the following enumerated paragraphs, may additionally or alternatively be referred to as a "step for" performing the recited action.

A1. A needle module for applying ink to skin of a subject, the needle module comprising:

a module housing that extends along and defines a housing axis and that includes a housing tip that defines a tip outlet, wherein the housing axis extends through the housing tip, and wherein the module housing includes and/or defines an ink reservoir, optionally wherein the ink reservoir is configured to contain a volume of ink to be applied to the skin of the subject; and a needle assembly operatively supported within the module housing;

wherein the needle assembly includes:

a drive bar extending at least partially along a drive bar axis; and a needle grouping extending from the drive bar at least partially along a needle grouping axis and terminating in one or more needles;

wherein the needle assembly is configured to reciprocate along the drive bar axis such that at least a portion of the needle grouping reciprocates into and out of the module housing via the tip outlet; wherein the needle grouping contacts the housing tip at a needle grouping contact location as the needle grouping reciprocates into and out of the module housing; and wherein the needle grouping is angled relative to the housing tip at the needle grouping contact location at least when the needle grouping extends out of the module housing.

A2. The needle module of paragraph A1, wherein the drive bar axis is at least substantially parallel to the housing axis; optionally wherein the drive bar axis is nominally fully parallel to the housing axis; and optionally wherein the drive bar axis is collinear with the housing axis.

A3. The needle module of any of paragraphs A1-A2, wherein the needle grouping is continuously and positively biased against the needle grouping contact location while the needle assembly reciprocates into and out of the module housing during operative use of the needle module.

A4. The needle module of any of paragraphs A1-A3, wherein the ink reservoir is configured to contain the volume of ink, and wherein the needle module is configured to facilitate a flow of the ink from the ink reservoir to the one or more needles via capillary action.

A5. The needle module of any of paragraphs A1-A4, wherein the needle assembly is configured to translate relative to the module housing along a direction at least substantially parallel to the drive bar axis to transition among a plurality of positions defined between and including a retracted position, in which the needle grouping is maximally received within the module housing, and an extended position, in which the one or more needles extend maximally distal the housing tip.

A6. The needle module of paragraph A5, wherein the needle assembly is biased toward the retracted position.

A7. The needle module of any of paragraphs A5-A6, wherein, when the needle assembly is in the retracted position, the one or more needles one or more of:

(i) are at least substantially, and optionally nominally fully, contained within the module housing;

(ii) do not extend beyond the housing tip; and (iii) are protected by the housing tip.

A8. The needle module of any of paragraphs A5-A7, wherein the drive bar includes a needle grouping attachment end and a reciprocating machine end; wherein the needle grouping extends from the needle grouping attachment end; and wherein the reciprocating machine end extends exterior of the module housing and is configured to receive a driving force from a reciprocating machine, optionally from a machine drive member of the reciprocating machine that engages the reciprocating machine end exterior of the module housing, to reciprocate the needle assembly between the retracted position and the extended position; and optionally wherein the reciprocating machine includes, and optionally is, one or more of a tattoo machine, a pen-style tattoo machine, a rotary tattoo machine, and a coil tattoo machine.

A9. The needle module of any of paragraphs A1-A8, wherein at least a portion of the needle grouping extends along the needle grouping axis at the needle grouping contact location.

A10. The needle module of any of paragraphs A1-A9, wherein the needle grouping contact location includes, and optionally is, one or more of:

(i) a single point of contact;

(ii) a discrete plurality of spaced-apart contact locations, optionally of spaced-apart single points of contact;

(iii) a region of contact that extends along a direction at least substantially perpendicular to the needle grouping axis; and (iv) a region of contact that extends along a direction at least substantially parallel to the needle grouping axis.

A11. The needle module of any of paragraphs A1-A10, wherein the housing tip defines a needle guide surface that includes the needle grouping contact location.

A12. The needle module of paragraph A11, wherein the needle guide surface extends along a direction at least substantially parallel to the housing axis.

A13. The needle module of any of paragraphs A11-A12, wherein the needle guide surface is curved along a direction perpendicular to the housing axis.

A14. The needle module of any of paragraphs A14-A13, wherein the needle guide surface includes, and optionally is, a flat surface.

A15. The needle module of any of paragraphs A1-A14, wherein the needle grouping contact location has a contact location longitudinal extent, as measured along a/the needle guide surface and in a direction at least substantially parallel to the housing axis; wherein the needle guide surface has a guide surface longitudinal extent, as measured along the needle guide surface and in a direction at least substantially parallel to the housing axis; and wherein the contact location longitudinal extent is one or more of at most 10% of the guide surface longitudinal extent, at most 5% of the guide surface longitudinal extent, and at most 1% of the guide surface longitudinal extent.

A16. The needle module of any of paragraphs A1-A15, wherein the needle grouping contact location is nominally fully stationary relative to the module housing while the needle assembly reciprocates relative to the module housing, optionally while at least a portion of the needle grouping extends out of the module housing.

A17. The needle module of any of paragraphs A1-A15, wherein the needle grouping contact location shifts relative to the module housing along a direction at least substantially parallel to the drive bar axis as the needle assembly reciprocates into and out of the module housing, optionally while at least a portion of the needle grouping extends out of the module housing.

A18. The needle module of any of paragraphs A1-A17, wherein the housing tip defines a contact location tangent plane that extends tangentially to one or both of the housing tip and a/the needle guide surface at the needle grouping contact location; and wherein the needle grouping contacts the housing tip with a housing contact angle, as measured between the needle grouping axis and the contact location tangent plane, that is one or more of at least 1 degree, at least 2 degrees, at least 3 degrees, at least 5 degrees, at most 10 degrees, at most 7 degrees, at most 5 degrees, at most 4 degrees, at most 2.5 degrees, and at most 1.5 degrees.

A19. The needle module of paragraph A18, wherein the contact location tangent plane is nominally fully parallel to the housing axis.

A20. The needle module of any of paragraphs A18-A19, wherein the contact location tangent plane intersects the housing axis.

A21. The needle module of any of paragraphs A18-A20, wherein the contact location tangent plane is one or both of:
(i) nominally fully parallel to a/the needle guide surface; and
(ii) nominally fully coplanar with the needle guide surface.

A22. The needle module of any of paragraphs A1-A21. wherein the needle grouping is operatively coupled to the drive bar such that the needle grouping axis deviates from the drive bar axis by a needle grouping bias angle, as measured between the needle grouping axis and the drive bar axis; and wherein the needle grouping bias angle is one or more of at least 1 degree, at least 2 degrees, at least 3 degrees, at least 5 degrees, at most 10 degrees, at most 7 degrees, at most 5 degrees, at most 4 degrees, at most 2.5 degrees, and at most 1.5 degrees.

A23. The needle module of any of paragraphs A1-A22, wherein the needle grouping extends along the needle grouping axis from a/the needle grouping attachment end of the drive bar to the one or more needles.

A24. The needle module of any of paragraphs A1-A22, wherein the needle grouping is one or both of bent and curved between the drive bar and the one or more needles about an axis that is perpendicular to the needle grouping axis.

A25. The needle module of any of paragraphs A1-A24, wherein the needle grouping axis is one or both of nominally fully parallel to the drive bar axis and collinear with the drive bar axis.

A26. The needle module of any of paragraphs A1-A25, wherein the needle grouping includes one or both of:
(i) a needle head that includes the one or more needles; and
(ii) a needle bar that is coupled to the drive bar, optionally directly coupled to the drive bar, and optionally coupled to a/the needle grouping attachment end of the drive bar.

A27. The needle module of paragraph A26, wherein the needle head is operatively attached to the needle bar.

A28. The needle module of paragraph A27, wherein at least a portion of the needle head is operatively coupled to the needle bar; optionally wherein at least a portion of the needle head is one or more of soldered to the needle bar, welded to the needle bar, bonded to the needle bar, adhesively bonded to the needle bar, and mechanically fastened to the needle bar.

A29. The needle module of paragraph A26, wherein at least a portion of the needle head and the needle bar are one or more of coextensive, monolithic, and integrally formed.

A30. The needle module of any of paragraphs A1-A29, wherein the one or more needles includes, and optionally consists of, one or more of 1 needle, at least 1 needle, at least 2 needles, at least 5 needles, at least 10 needles, at least 15 needles, at least 20 needles, at least 25 needles, at least 30 needles, at most 35 needles, at most 27 needles, at most 22 needles, at most 17 needles, at most 12 needles, at most 7 needles, and at most 3 needles.

A31. The needle module of any of paragraphs A1-A30, wherein the one or more needles includes a plurality of needles arranged in a circularly clustered configuration.

A32. The needle module of any of paragraphs A1-A31, wherein the one or more needles includes a plurality of needles arranged in a linear configuration.

A33. The needle module of paragraph A32, wherein the one or more needles includes a first needle subset and a second needle subset; wherein each of the first needle subset and the second needle subset includes a plurality of needles arranged in a linear configuration.

A34. The needle module of paragraph A33, wherein each needle of the first needle subset extends nominally fully parallel to each other needle of the first needle subset; and wherein each needle of the second needle subset extends nominally fully parallel to each other needle of the second needle subset.

A35. The needle module of any of paragraphs A33-A34, wherein each needle of the first needle subset extends nominally fully parallel to each needle of the second needle subset.

A36. The needle module of any of paragraphs A33-A35, wherein each needle of the first needle subset extends nominally fully parallel to a/the needle bar.

A37. The needle module of any of paragraphs A33-A36, wherein each needle of the first needle subset contacts the needle grouping contact location.

A38. The needle module of any of paragraphs A33-A37, wherein the housing tip includes a needle retainer that faces a/the needle guide surface; and wherein each needle of the second needle subset contacts the needle retainer.

A39. The needle module of paragraph A38, wherein the first needle subset and the second needle subset are biased apart from one another such that, as the needle assembly reciprocates into and out of the module housing, each needle of the first needle subset is continually urged into contact with the needle guide surface and each needle of the second needle subset is continually urged into contact with the needle retainer.

A40. The needle module of any of paragraphs A1-A39, wherein the drive bar is one or both of bent and curved between a/the reciprocating machine end and a/the needle grouping attachment end and about an axis that is perpendicular to the drive bar axis.

A41. The needle module of any of paragraphs A1-A40, wherein the module housing includes a drive end opposite the housing tip; and wherein the drive bar extends at least partially out of the drive end.

A42. The needle module of paragraph A41, further comprising a housing cap that is operatively coupled to the drive end; optionally wherein the housing cap engages the drive bar at least when the needle assembly is in the retracted position.

A43. The needle module of paragraph A42, wherein the housing cap includes a drive bar receiver that receives and engages the drive bar at least when the needle assembly is in the retracted position.

A44. The needle module of paragraph A43, wherein the drive bar receiver is configured to engage the drive bar to orient the drive bar in a nominal drive bar orientation such that one or both of:

(i) the drive bar axis is nominally fully parallel to the housing axis at least when the needle assembly is in the retracted position; and (ii) the drive bar assumes an angular orientation relative to the housing axis such that the needle grouping contacts a/the needle guide surface at least when the needle assembly is in the retracted position.

A45. The needle module of paragraph A44, wherein the drive bar includes a drive bar locator; and wherein the drive bar receiver is configured to engage the drive bar locator at least when the needle assembly is in the retracted position to maintain the drive bar in the nominal drive bar orientation.

A46. The needle module of paragraph A45, wherein the drive bar locator has a cross-sectional shape, as viewed in a plane perpendicular to the drive bar axis, that is the same as at least a portion of a cross-sectional shape of the drive bar receiver, optionally wherein each of the drive bar locator and the drive bar receiver has a cross-sectional shape that is one or more of triangular, rectangular, square, at least partially flat, and non-circular.

A47. The needle module of any of paragraphs A1-A46, further comprising a biasing member that biases the needle assembly toward a/the retracted position.

A48. The needle module of paragraph A47, wherein the biasing member is an elastic biasing member that is operatively coupled to each of a/the housing cap and the needle assembly and that resiliently deforms as the needle assembly reciprocates between the retracted position and the extended position.

A49. The needle module of any of paragraphs A47-A48, wherein the biasing member includes, and optionally is, a diaphragm that is operatively coupled to each of the housing cap and the needle assembly; and wherein the diaphragm fluidly separates the ink reservoir from the housing cap.

A50. The needle module of any of paragraphs A1-A49, wherein the module housing defines a reservoir opening that permits access to the ink reservoir; optionally wherein the reservoir opening is at least partially spaced apart from one or both of the housing tip and the tip outlet.

A51. The needle module of paragraph A50, wherein the reservoir opening includes, and optionally is, one or more of a hole, an aperture, a cutout, a channel, and a groove.

A52. The needle module of any of paragraphs A1-A51, wherein the module housing is at least substantially cylindrical.

A53. The needle module of any of paragraphs A1-A52, wherein the module housing is configured to be at least partially received within a/the reciprocating machine during operative use of the needle module.

A54. The needle module of any of paragraphs A1-A53, wherein the needle module is free from structures that engage one or both of the needle grouping and the drive bar to urge the needle grouping into contact with the housing tip.

A55. The needle module of paragraph A54, wherein the needle module is free from structures that extend from, project from, and/or are operatively coupled to the module housing and that contact the needle assembly other than at the needle grouping contact location in a manner that biases the needle grouping toward the needle grouping contact location.

A56. The needle module of any of paragraphs A1-A55, wherein the needle module is one or more of a liner module, a shader module, a round shader module, a flat shader module, a magnum shader module, and a hybrid module.

B1. A method of assembling a needle module, comprising:

preparing a needle assembly that includes a needle grouping operatively coupled to a drive bar; and installing the needle assembly within a module housing such that at least a portion of the needle grouping is configured to reciprocate into and out of the module housing and such that the needle grouping contacts the module housing at a needle grouping contact location as the needle grouping reciprocates into and out of the module housing.

B2. The method of paragraph B1, wherein the preparing the needle assembly includes operatively coupling the needle grouping to the drive bar.

B3. The method of any of paragraphs B1-B2, wherein the preparing the needle assembly includes preparing such that at least a portion of the needle grouping extends along a needle grouping axis that deviates from a drive bar axis along which at least a portion of the drive bar extends by a needle grouping bias angle, as measured between the needle grouping axis and the drive bar axis.

B4. The method of paragraph B3, wherein the preparing the needle assembly includes configuring the needle assembly such that needle grouping bias angle is one or more of at least 1 degree, at least 2 degrees, at least 3 degrees, at least 5 degrees, at most 10 degrees, at most 7 degrees, at most 5 degrees, at most 4 degrees, at most 2.5 degrees, and at most 1.5 degrees.

B5. The method of any of paragraphs B1-B4, when dependent from paragraph B2, wherein the operatively coupling the needle grouping to the drive bar includes coupling such that the needle grouping extends away from a needle grouping attachment end of the drive bar along a direction that is angled relative to a portion of the drive bar adjacent to the needle grouping attachment end, optionally by a/the needle grouping bias angle.

B6. The method of any of paragraphs B1-B5, wherein the preparing the needle assembly includes bending the drive bar such that a portion of the drive bar extends along a direction that is one or both of curved and angled relative to the drive bar axis.

B7. The method of paragraph B6, wherein the bending the drive bar is performed prior to the operatively coupling the needle grouping to the drive bar.

B8. The method of paragraph B6, wherein the bending the drive bar is performed subsequent to the operatively coupling the needle grouping to the drive bar.

B9. The method of any of paragraphs B1-B8, wherein the preparing the needle assembly includes bending the needle grouping such that a portion of the needle grouping extends along a direction that is one or both of curved and angled relative to the needle grouping axis.

B10. The method of paragraph B9, wherein the bending the needle grouping is performed prior to the operatively coupling the needle grouping to the drive bar.

B11. The method of paragraph B9, wherein the bending the needle grouping is performed subsequent to the operatively coupling the needle grouping to the drive bar.

B12. The method of any of paragraphs B1-B11, wherein the preparing the needle assembly is performed prior to the installing the needle assembly within the module housing.

B13. The method of any of paragraphs B1-B12, wherein the needle module is the needle module of any of paragraphs A1-A56.

INDUSTRIAL APPLICABILITY

The needle modules and methods disclosed herein are applicable to the tattoo and permanent makeup industries.

It is believed that the disclosure set forth above encompasses multiple distinct inventions with independent utility. While each of these inventions has been disclosed in its preferred form, the specific embodiments thereof as disclosed and illustrated herein are not to be considered in a limiting sense as numerous variations are possible. The subject matter of the inventions includes all novel and non-obvious combinations and subcombinations of the various elements, features, functions and/or properties disclosed herein. Similarly, where the claims recite "a" or "a first" element or the equivalent thereof, such claims should be understood to include incorporation of one or more such elements, neither requiring nor excluding two or more such elements.

It is believed that the following claims particularly point out certain combinations and subcombinations that are directed to one of the disclosed inventions and are novel and non-obvious. Inventions embodied in other combinations and subcombinations of features, functions, elements, and/or properties may be claimed through amendment of the present claims or presentation of new claims in this or a related application. Such amended or new claims, whether they are directed to a different invention or directed to the same invention, whether different, broader, narrower, or equal in scope to the original claims, are also regarded as included within the subject matter of the inventions of the present disclosure.

The invention claimed is:

1. A needle module for applying ink to skin of a subject, the needle module comprising:
   a module housing that extends along and defines a housing axis and that includes a housing tip that defines a tip outlet, wherein the housing axis extends through the housing tip, and wherein the module housing includes an ink reservoir; and
   a needle assembly operatively supported within the module housing;
   wherein the needle assembly includes:
   a drive bar extending at least partially along a drive bar axis; and
   a needle grouping extending from the drive bar at least partially along a needle grouping axis and terminating in one or more needles;
   wherein the needle assembly is configured to reciprocate along the drive bar axis such that at least a portion of the needle grouping reciprocates into and out of the module housing via the tip outlet; wherein the needle grouping contacts the housing tip at a needle grouping contact location as the needle grouping reciprocates into and out of the module housing; wherein the needle grouping is angled relative to the housing tip at the needle grouping contact location at least when the needle grouping extends out of the module housing; wherein the needle assembly is configured to translate relative to the module housing along a direction at least substantially parallel to the drive bar axis to transition among a plurality of positions defined between and including a retracted position, in which the needle grouping is maximally received within the module housing, and an extended position, in which the one or more needles extend maximally distal the housing tip; wherein the needle assembly is biased toward the retracted position; and wherein the needle grouping is continuously and positively biased against the needle grouping contact location while the needle assembly reciprocates into and out of the module housing during operative use of the needle module; wherein the needle grouping is operatively coupled to the drive bar such that the needle grouping axis deviates from the drive bar axis by a needle grouping bias angle, as measured between the needle grouping axis and the drive bar axis, that is at least 1 degree and at most 5 degrees; and wherein the needle grouping extends along the needle grouping axis from a needle grouping attachment end of the drive bar to the one or more needles.

2. A needle module for applying ink to skin of a subject, the needle module comprising:
   a module housing that extends along and defines a housing axis and that includes a housing tip that defines a tip outlet, wherein the housing axis extends through the housing tip, and wherein the module housing includes an ink reservoir; and
   a needle assembly operatively supported within the module housing;
   wherein the needle assembly includes:
   a drive bar extending at least partially along a drive bar axis; and
   a needle grouping extending from the drive bar at least partially along a needle grouping axis and terminating in one or more needles; and
   wherein the needle assembly is configured to reciprocate along the drive bar axis such that at least a portion of the needle grouping reciprocates into and out of the module housing via the tip outlet; wherein the needle grouping contacts the housing tip at a needle grouping contact location as the needle grouping reciprocates into and out of the module housing; wherein the needle grouping is angled at a non-zero angle relative to the housing tip at the needle grouping contact location at least when the needle grouping extends out of the module housing; and wherein the needle grouping is one or both of bent and curved between the drive bar and the one or more needles about an axis that is perpendicular to the needle grouping axis.

3. The needle module of claim 2, wherein the needle assembly is configured to translate relative to the module housing along a direction at least substantially parallel to the drive bar axis to transition among a plurality of positions defined between and including a retracted position, in which the needle grouping is maximally received within the module housing, and an extended position, in which the one or more needles extend maximally distal the housing tip; wherein the needle assembly is biased toward the retracted position; and wherein the needle grouping is continuously and positively biased against the needle grouping contact location while the needle assembly reciprocates into and out of the module housing during operative use of the needle module.

4. The needle module of claim 2, wherein at least a portion of the needle grouping extends along the needle grouping axis at the needle grouping contact location.

5. The needle module of claim 2, wherein the needle grouping contact location includes one or more of:
   (i) a single point of contact;
   (ii) a discrete plurality of spaced-apart contact locations;

(iii) a region of contact that extends along a direction at least substantially perpendicular to the needle grouping axis; and (iv) a region of contact that extends along a direction at least substantially parallel to the needle grouping axis.

6. The needle module of claim 2, wherein the housing tip defines a needle guide surface that includes the needle grouping contact location; wherein the needle grouping contact location has a contact location longitudinal extent, as measured along the needle guide surface and in a direction at least substantially parallel to the housing axis; wherein the needle guide surface has a guide surface longitudinal extent, as measured along the needle guide surface and in a direction at least substantially parallel to the housing axis; and wherein the contact location longitudinal extent is at most 5% of the guide surface longitudinal extent.

7. The needle module of claim 2, wherein the needle grouping contact location shifts relative to the module housing along a direction at least substantially parallel to the drive bar axis as the needle assembly reciprocates into and out of the module housing.

8. The needle module of claim 2, wherein the housing tip defines a needle guide surface that includes the needle grouping contact location; wherein the housing tip defines a contact location tangent plane that extends tangentially to one or both of the housing tip and the needle guide surface at the needle grouping contact location; and wherein the needle grouping contacts the housing tip with a housing contact angle, as measured between the needle grouping axis and the contact location tangent plane, that is at least 1 degree and at most 5 degrees.

9. The needle module of claim 2, wherein the needle grouping is operatively coupled to the drive bar such that the needle grouping axis deviates from the drive bar axis by a needle grouping bias angle, as measured between the needle grouping axis and the drive bar axis, that is at least 1 degree and at most 5 degrees.

10. The needle module of claim 2, wherein the needle grouping extends along the needle grouping axis from a needle grouping attachment end of the drive bar to the one or more needles.

11. The needle module of claim 2, wherein the drive bar is one or both of bent and curved between a reciprocating machine end of the drive bar and a needle grouping attachment end of the drive bar and about an axis that is perpendicular to the drive bar axis.

12. The needle module of claim 2, wherein the needle assembly is configured to translate relative to the module housing along a direction at least substantially parallel to the drive bar axis to transition among a plurality of positions defined between and including a retracted position, in which the needle grouping is maximally received within the module housing, and an extended position, in which the one or more needles extend maximally distal the housing tip; wherein the module housing includes a drive end opposite the housing tip; wherein the drive bar extends at least partially out of the drive end; wherein the needle module further comprises a housing cap that is operatively coupled to the drive end; wherein the housing cap engages the drive bar at least when the needle assembly is in the retracted position; wherein the housing cap includes a drive bar receiver that receives and engages the drive bar at least when the needle assembly is in the retracted position; and wherein the drive bar receiver is configured to engage the drive bar to orient the drive bar in a nominal drive bar orientation such that:

(i) the drive bar axis is nominally fully parallel to the housing axis at least when the needle assembly is in the retracted position; and (ii) the drive bar assumes an angular orientation relative to the housing axis such that the needle grouping contacts a needle guide surface of the module housing at least when the needle assembly is in the retracted position.

13. The needle module of claim 12, wherein the drive bar includes a drive bar locator; and wherein the drive bar receiver is configured to engage the drive bar locator at least when the needle assembly is in the retracted position to maintain the drive bar in the nominal drive bar orientation.

14. The needle module of claim 2, wherein the needle assembly is configured to translate relative to the module housing along a direction at least substantially parallel to the drive bar axis to transition among a plurality of positions defined between and including a retracted position, in which the needle grouping is maximally received within the module housing, and an extended position, in which the one or more needles extend maximally distal the housing tip; wherein the module housing includes a drive end opposite the housing tip; wherein the drive bar extends at least partially out of the drive end; and wherein the needle module further comprises:

a housing cap that is operatively coupled to the drive end; and an elastic biasing member that biases the needle assembly toward the retracted position;

wherein the biasing member is operatively coupled to each of the housing cap and the needle assembly and resiliently deforms as the needle assembly reciprocates between the retracted position and the extended position.

15. The needle module of claim 2, wherein the needle module is free from structures that engage one or both of the needle grouping and the drive bar to urge the needle grouping into contact with the housing tip.

16. A method of assembling the needle module of claim 2, comprising:

preparing the needle assembly; and installing the needle assembly within the module housing;

wherein the preparing the needle assembly includes preparing such that the at least a portion of the needle grouping extends along the needle grouping axis that deviates from the drive bar axis along which at least a portion of the drive bar extends by a needle grouping bias angle, as measured between the needle grouping axis and the drive bar axis, that is at least 1 degree and at most 5 degrees; and wherein the preparing the needle assembly is performed prior to the installing the needle assembly within the module housing.

17. The method of claim 16, wherein the preparing the needle assembly includes operatively coupling the needle grouping to the drive bar such that the needle grouping extends away from a needle grouping attachment end of the drive bar along a direction that is angled relative to a portion of the drive bar adjacent to the needle grouping attachment end by the needle grouping bias angle.

18. The method of claim 16, wherein the preparing the needle assembly includes bending the drive bar such that a portion of the drive bar extends along a direction that is one or both of curved and angled relative to the drive bar axis.

19. The method of claim 16, wherein the preparing the needle assembly includes bending the needle grouping such that a portion of the needle grouping extends along a direction that is one or both of curved and angled relative to the needle grouping axis.

20. A needle module for applying ink to skin of a subject, the needle module comprising:
   a module housing that extends along and defines a housing axis and that includes a housing tip that defines a tip outlet, wherein the housing axis extends through the housing tip, and wherein the module housing includes an ink reservoir; and
   a needle assembly operatively supported within the module housing;
   wherein the needle assembly includes:
      a drive bar extending at least partially along a drive bar axis; and
      a needle grouping extending from the drive bar at least partially along a needle grouping axis and terminating in one or more needles; and
   wherein the needle assembly is configured to reciprocate along the drive bar axis such that at least a portion of the needle grouping reciprocates into and out of the module housing via the tip outlet; wherein the needle grouping contacts the housing tip at a needle grouping contact location as the needle grouping reciprocates into and out of the module housing; wherein the needle grouping is angled at a non-zero angle relative to the housing tip at the needle grouping contact location at least when the needle grouping extends out of the module housing; wherein the housing tip defines a needle guide surface that includes the needle grouping contact location; wherein the needle grouping contact location has a contact location longitudinal extent, as measured along the needle guide surface and in a direction at least substantially parallel to the housing axis; wherein the needle guide surface has a guide surface longitudinal extent, as measured along the needle guide surface and in a direction at least substantially parallel to the housing axis; and wherein the contact location longitudinal extent is at most 5% of the guide surface longitudinal extent.

21. A needle module for applying ink to skin of a subject, the needle module comprising:
   a module housing that extends along and defines a housing axis and that includes a housing tip that defines a tip outlet, wherein the housing axis extends through the housing tip, and wherein the module housing includes an ink reservoir; and
   a needle assembly operatively supported within the module housing;
   wherein the needle assembly includes:
      a drive bar extending at least partially along a drive bar axis; and
      a needle grouping extending from the drive bar at least partially along a needle grouping axis and terminating in one or more needles; and
   wherein the needle assembly is configured to reciprocate along the drive bar axis such that at least a portion of the needle grouping reciprocates into and out of the module housing via the tip outlet; wherein the needle grouping contacts the housing tip at a needle grouping contact location as the needle grouping reciprocates into and out of the module housing; wherein the needle grouping is angled at a non-zero angle relative to the housing tip at the needle grouping contact location at least when the needle grouping extends out of the module housing; and wherein the needle module is free from structures that engage one or both of the needle grouping and the drive bar to urge the needle grouping into contact with the housing tip.

* * * * *